US012779068B2

(12) United States Patent
Shane et al.

(10) Patent No.: US 12,779,068 B2
(45) Date of Patent: Nov. 3, 2026

(54) DEVICE, SYSTEMS, AND METHODS FOR ENHANCED IONIZED HYDROGEN PEROXIDE DECONTAMINATION

(71) Applicant: TOMI ENVIRONMENTAL SOLUTIONS, INC., Frederick, MD (US)

(72) Inventors: Halden Stuart Shane, Beverly Hills, CA (US); Elissa J. Shane, Frederick, MD (US); Johnny Sullivan Cato, Lynwood, CA (US)

( * ) Notice: Subject to any disclaimer, the term of this patent is extended or adjusted under 35 U.S.C. 154(b) by 313 days.

(21) Appl. No.: 18/621,808

(22) Filed: Mar. 29, 2024

(65) Prior Publication Data

US 2024/0325581 A1 Oct. 3, 2024

Related U.S. Application Data

(60) Provisional application No. 63/612,560, filed on Dec. 20, 2023, provisional application No. 63/601,515, filed on Nov. 21, 2023, provisional application No. 63/492,905, filed on Mar. 29, 2023.

(51) Int. Cl.
*A61L 2/14* (2006.01)
*A61L 2/24* (2006.01)

(52) U.S. Cl.
CPC .................. *A61L 2/14* (2013.01); *A61L 2/24* (2013.01); *A61L 2202/11* (2013.01); *A61L 2202/14* (2013.01); *A61L 2202/15* (2013.01); *A61L 2202/16* (2013.01)

(58) Field of Classification Search
CPC .................................... A61L 2/24; A61L 2/14
See application file for complete search history.

(56) References Cited

U.S. PATENT DOCUMENTS

| | | | | |
|---|---|---|---|---|
| 10,391,188 | B2 | 8/2019 | Shane et al. | |
| 2011/0135537 | A1 | 6/2011 | Schwartz et al. | |
| 2011/0284596 | A1 | 11/2011 | Sventitsky et al. | |
| 2015/0202339 | A1 | 7/2015 | Schwartz et al. | |
| 2019/0247529 | A1 * | 8/2019 | Shane | A61L 2/22 |
| 2020/0345021 | A1 | 11/2020 | Shane | |
| 2021/0069360 | A1 | 3/2021 | Shane et al. | |

FOREIGN PATENT DOCUMENTS

CN 107750087 * 3/2018

OTHER PUBLICATIONS

English machine translation of CN 107750087 Liu et al. (Year: 2018).*
International Search Report and Written Opinion of International Application No. PCT /US2024/022404 mailed Sep. 4, 2024.

* cited by examiner

*Primary Examiner* — Donald R Spamer

(57) ABSTRACT

The Applicant has improved the efficacy of breaking the double bond of its cleaning solution by redesigning the following aspects. Lowering the electrode posts in the applicator and changing the arc's power source from AC voltage to DC voltage. Lowering the electrode posts puts the arc discharge into a more effective position for activating the cleaning solution prior to dispersion into the treatment area. Changing the arc's power source from AC voltage to DC voltage increases the homogenous charge characteristics of the droplets. This causes a greater percentage of the droplets to repel each other and seek equilibrium. It also increases air ionization, making it easier for the charged droplets to contact surfaces.

13 Claims, 24 Drawing Sheets

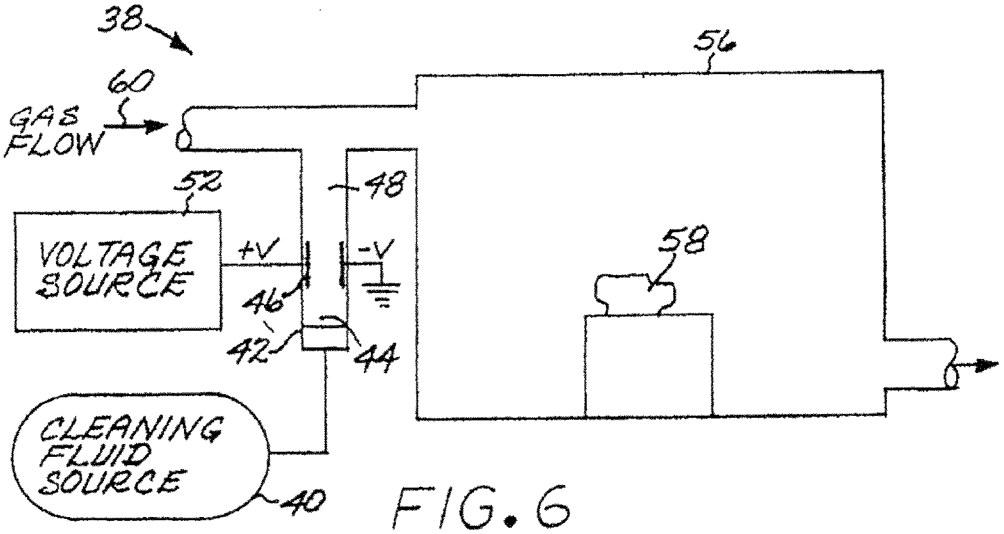
FIG. 6
FIG. 7
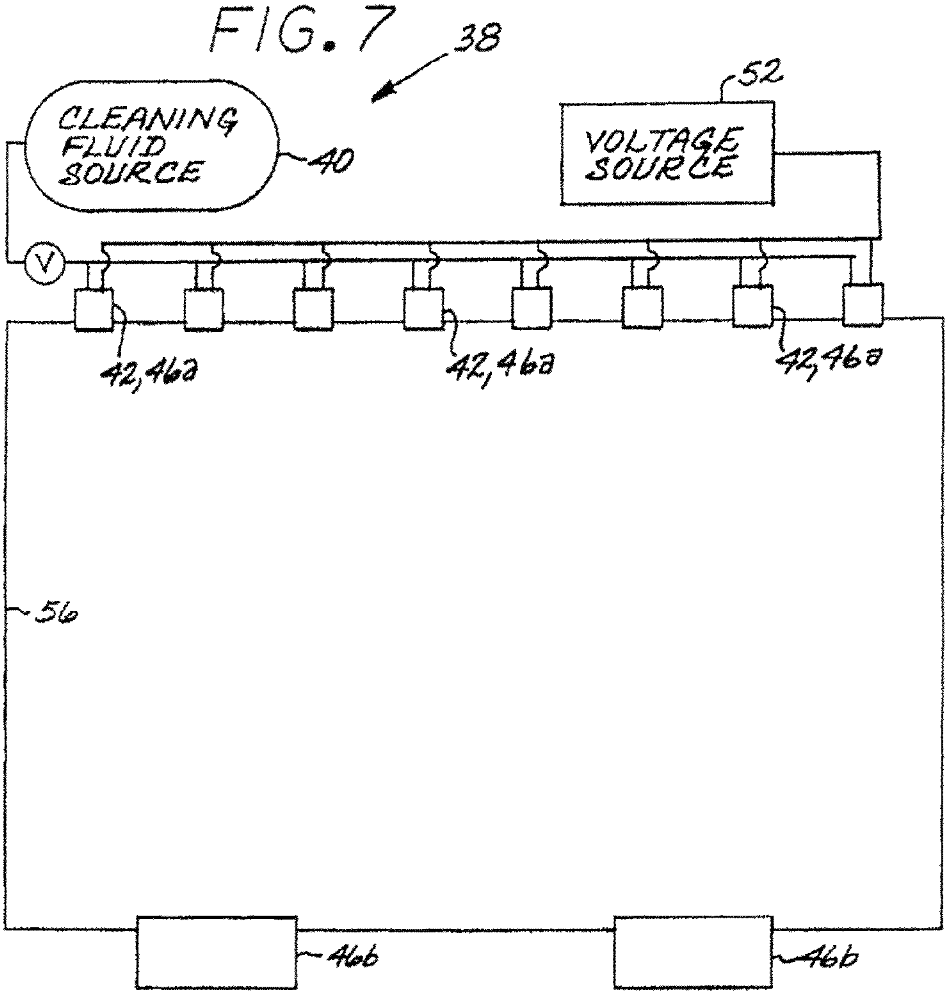

DEVICE, SYSTEMS, AND METHODS FOR ENHANCED IONIZED HYDROGEN PEROXIDE DECONTAMINATION

This application claims priority from U.S. Provisional Patent Application No. 63/492,905, filed Mar. 29, 2023; 63/601,515, filed Nov. 21, 2023; 63/612,560, filed Dec. 20, 2023, which are incorporated herein by reference.

FIELD

The present application relates generally to a multi-configuration system for decontaminating articles, enclosed spaces, and unenclosed spaces and, more particularly, to microbiological decontamination of such locations.

BACKGROUND

Microbial species are widely distributed in our environment. Most microbial species are of little concern, because they do not damage other living organisms. However, other microbiological species may infect man or animals and cause them harm. The removal of micro-organisms and decontamination of articles and spaces therefrom has long been of interest. Drugs and medical devices are sterilized and packaged in sterile containers. Medical environments such as operating rooms, wards, and examination rooms are decontaminated by various cleaning procedures so that micro-organisms of concern cannot spread from one patient to another.

Many available technologies for controlling micro-organisms are of value in the context of biological warfare and bioterrorism. Furthermore, existing decontamination technologies are limited in their effectiveness in tightly enclosed environments.

SUMMARY

Aspects of the application are methods, systems and devices for enhanced decontamination using ionized hydrogen peroxide by lowering the position of the electrodes of the posts generating a cold plasma arc and using a DC voltage source.

An aspect of the application is a method for decontaminating an article or substantially enclosed space, comprising the steps of: shearing a cleaning fluid into a mist comprising aerosol droplets accumulating in a top chamber portion of a substantially closed chamber comprising a funnel shaped top chamber portion, a bottom chamber portion, a side chamber portion and an interior chamber portion, wherein the cleaning fluid is sheared by ultrasonic cavitation; subjecting the mist to a nonthermal plasma actuator to form plasma activated ionic particles, wherein the actuator has posts generating a cold plasma arc; and contacting the article or substantially enclosed space to the plasma activated ionic particles, enhancing decontamination by ionized hydrogen peroxide by lowering the position of the electrodes of the posts generating a cold plasma arc and using a DC voltage source.

An aspect of the application is a method for decontaminating an article, surface or substantially enclosed space, comprising the steps of: shearing a cleaning fluid into a mist comprising aerosol droplets by cavitating the cleaning fluid using an ultrasonic cavitator submerged in a substantially closed chamber comprising the cleaning fluid; subjecting the mist to a nonthermal plasma actuator in an outlet tube extending from an opening in a top chamber portion of the substantially closed chamber, wherein the outlet tube comprises a hollow lumen with a distal opening above the top chamber portion for expelling the aerosol droplets to form plasma activated ionic particles; and contacting the article, surface, or substantially enclosed space with the plasma activated ionic particles, enhancing decontamination by ionized hydrogen peroxide by lowering the position of the electrodes of the posts generating a cold plasma arc and using a DC voltage source.

An aspect of the application is a method for decontaminating a small enclosure, comprising the steps of: entering input parameters of the small enclosure into a processing unit, wherein the processing unit is programmed to determine fluid properties of a cleaning fluid in a decontamination device based on the input parameters of the small enclosure space, activating a decontamination cycle of the decontamination device, wherein the decontamination cycle comprises the steps of: providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the substantially small enclosure, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by lowering the position of the electrodes of the posts generating a cold plasma arc and using a DC voltage source.

In certain embodiments, the user is operating the decontamination device manually. In certain embodiments, the decontamination device is hand-held to be operated manually. In certain embodiments, the input parameters of the small enclosure comprise: dimensions of the small enclosure space, a position of the decontamination device relative to boundaries of the small enclosure space, air temperature, pressure, and humidity of the small enclosure. In certain embodiments, the set fluid properties of the cleaning fluid comprise air pressure and fluid flow rate. In certain embodiments, the air valve is controlled by programming the processing unit to control a potentiometer. In certain embodiments, the determined fluid properties of the cleaning fluid are adjusted by a size and a shape of a tube located at an exit of the cleaning fluid out of the decontamination device. In certain embodiments, the very dry mist comprises particles of diameter size in the range of 0.1-0.7 microns. In certain embodiments, the fluid properties of the cleaning fluid are set by lowering the air pressure and the fluid flow rate respectively below a predetermined standard air pressure and a predetermined standard fluid flow rate. In certain embodiments, use includes entering input parameters of a small enclosure into a processing unit, wherein the processing unit is further programmed to determine the fluid properties of the cleaning fluid in the decontamination device based on the input parameters of the small enclosure. In certain embodiments, the very dry mist comprises particles of diameter size in the range of 0.1-0.7 microns. In certain embodiments, the input parameters of the small enclosure are manually input. In certain embodiments, the input parameters of the small enclosure are measured by a plurality of sensors that are in networked communication with the processing unit. In certain embodiments, the processing unit and the decontamination device are in wireless communication.

An aspect of the application is a system for decontaminating a small enclosure, comprising a decontamination device and a computer processor, wherein the computer processor is in networked communication with the decontamination device, wherein input parameters of the small enclosure space are entered into the computer processor, wherein the computer processor is programmed to determine fluid properties of a cleaning fluid in the decontamination device based on the input parameters of the small enclosure space, wherein the computer processor is further programmed to activate a decontamination cycle of the decontamination device, the decontamination cycle comprising the steps of: providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the substantially small enclosure space, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by lowering the position of the electrodes of the posts generating a cold plasma arc and using a DC voltage source.

In certain embodiments, the decontamination device is operated manually. In certain embodiments, the decontamination device is hand-held to be operated manually.

An aspect of the application is a method for decontaminating spaces, the method comprising the steps of: entering input parameters of a space into a processing unit, wherein the processing unit is programmed to determine fluid properties of a decontamination fluid in an ionization/aerosolization and activation device based on the input parameters of the space containing said fresh produce, wherein the decontamination fluid comprises hydrogen peroxide, activating a decontamination cycle of the ionization/aerosolization and activation device, wherein the decontamination cycle comprises the steps of: providing a reservoir of the decontamination fluid; setting the determined fluid properties of the decontamination fluid; generating a very dry mist comprising ionized/aerosolized hydrogen peroxide of the decontamination fluid, wherein an ionized/aerosolized mist of hydrogen peroxide of the decontamination fluid is passed through a cold plasma arc, wherein the mist is ionized by the cold plasma arc so that the mist comprises ionized/aerosolized particles in the nanosized range of mean diameter 40.3 nm, a mode of 33.4 nm and a standard deviation of 30.9 nm, and the very dry mist is a mist in which particles have particle size diameter within the ranges of 0.1-0.9 microns; applying the generated very dry mist to surfaces within the space, wherein the ionized/aerosolized hydrogen peroxide dissociates to form diatomic oxygen and water on the surfaces, and wherein after thirty minutes from passing through the cold plasma arc into the space containing fresh produce the ionized/aerosolized particles in the nanosized range continue to persist in the space containing fresh produce, enhancing decontamination by ionized hydrogen peroxide by lowering the position of the electrodes of the posts generating a cold plasma arc and using a DC voltage source.

BRIEF DESCRIPTION OF THE DRAWINGS

FIG. 6 illustrates a chamber-based decontamination apparatus.

FIG. 7 illustrates a decontamination apparatus for decontaminating a room.

Figure 1:
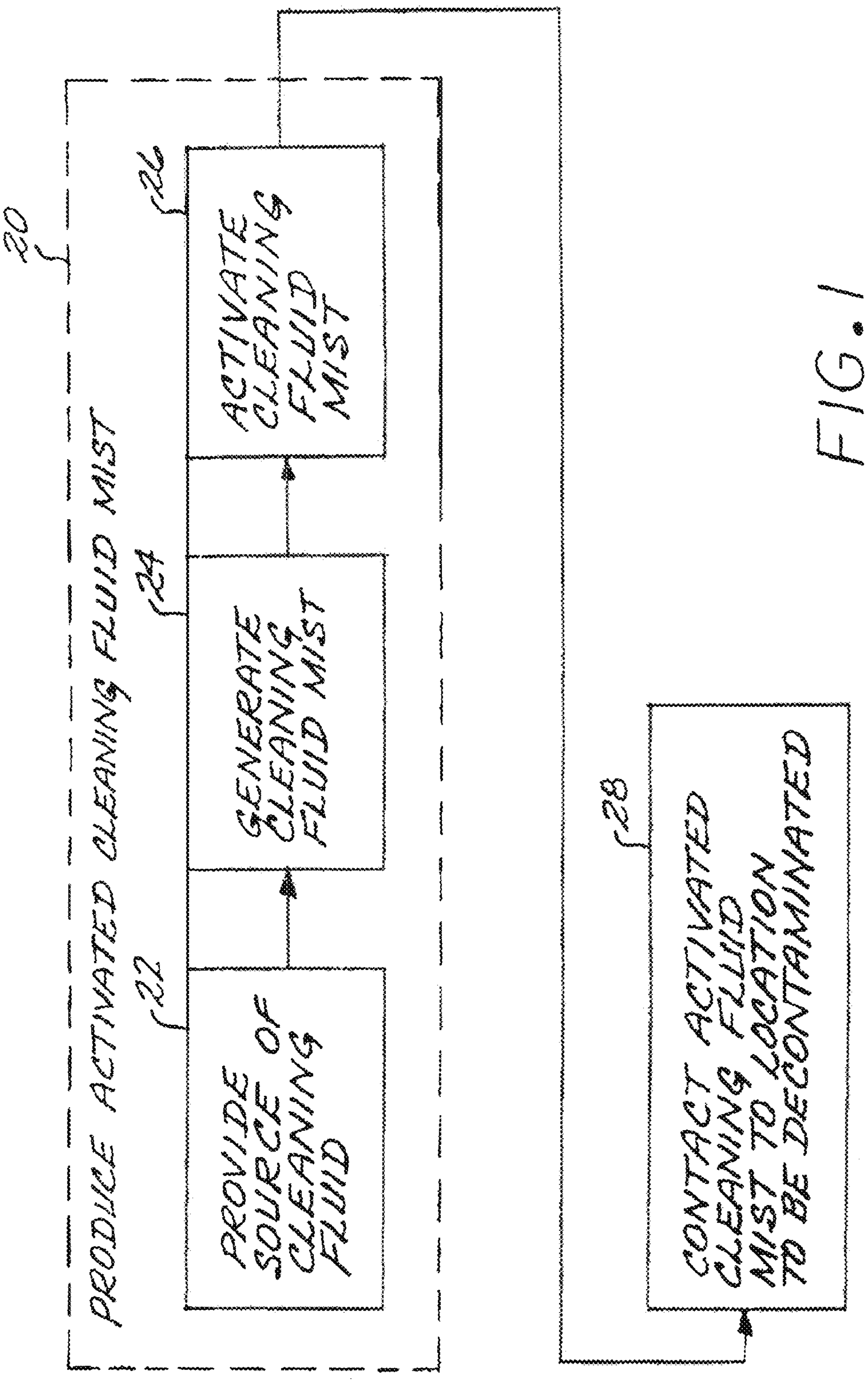
FIG. 1 is a block flow diagram of a general approach for denaturing a biochemical agent using an activated cleaning fluid mist.
Figure 2:
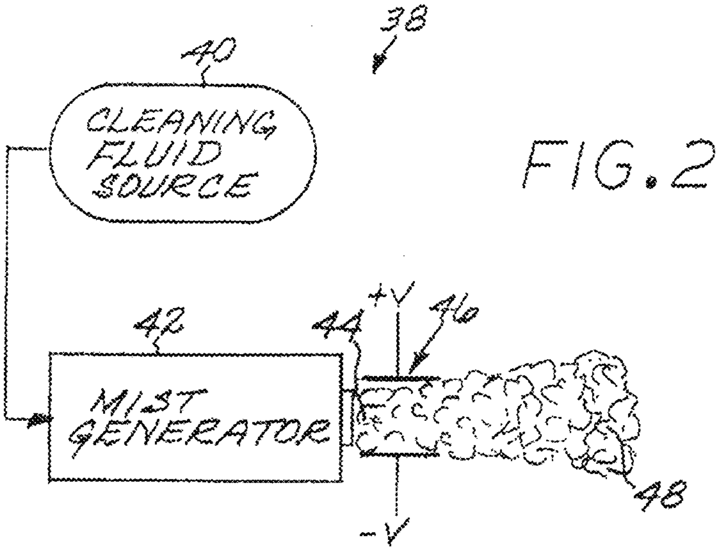
FIG. 2 is a schematic view of a first embodiment of apparatus for denaturing biological agents, with the activator proximally located to the mist generator.
Figure 3:
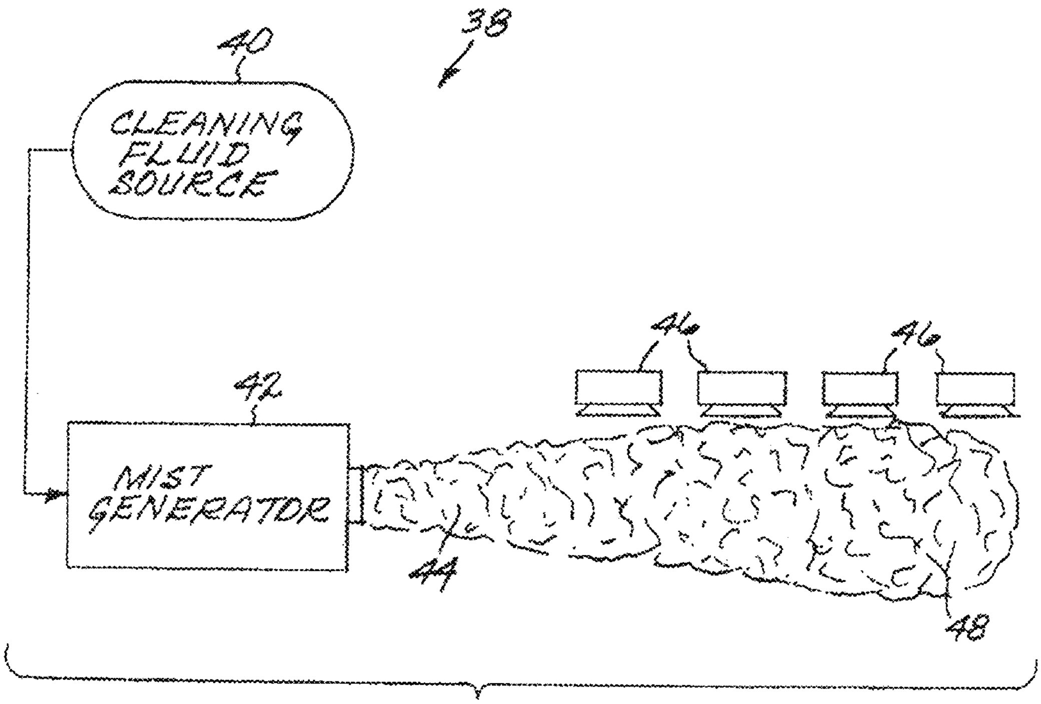
FIG. 3 is a schematic view of a second embodiment of apparatus for denaturing biological agents, with the activator located remotely from the mist generator.
Figure 4:
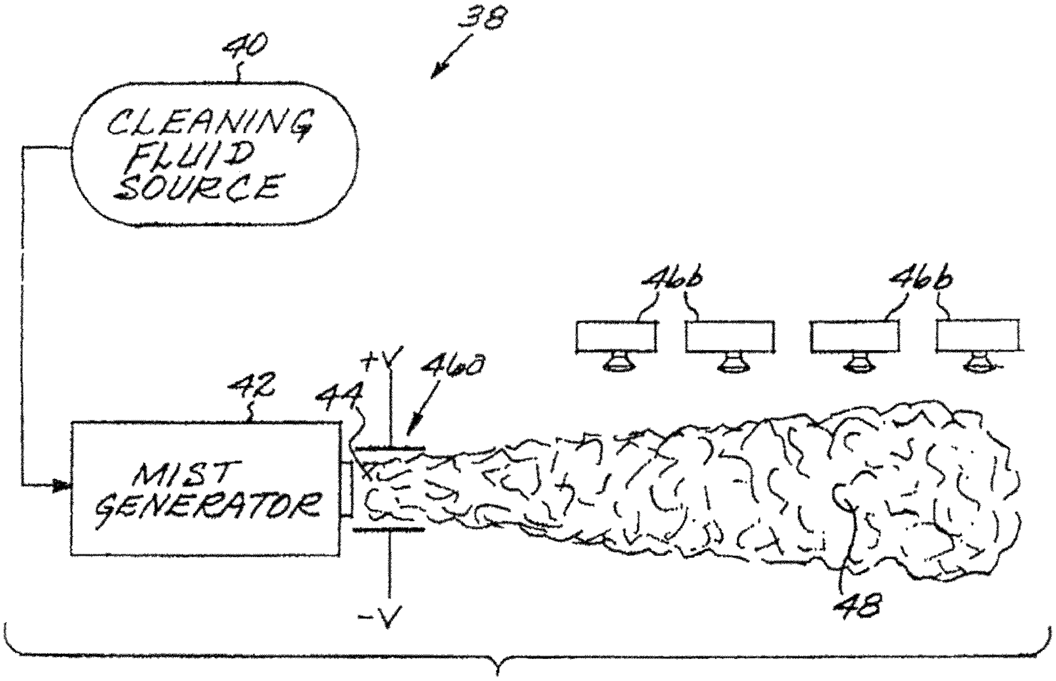
FIG. 4 is a schematic view of a third embodiment of apparatus for denaturing biological agents, with both proximate and remote activators.
Figure 5:
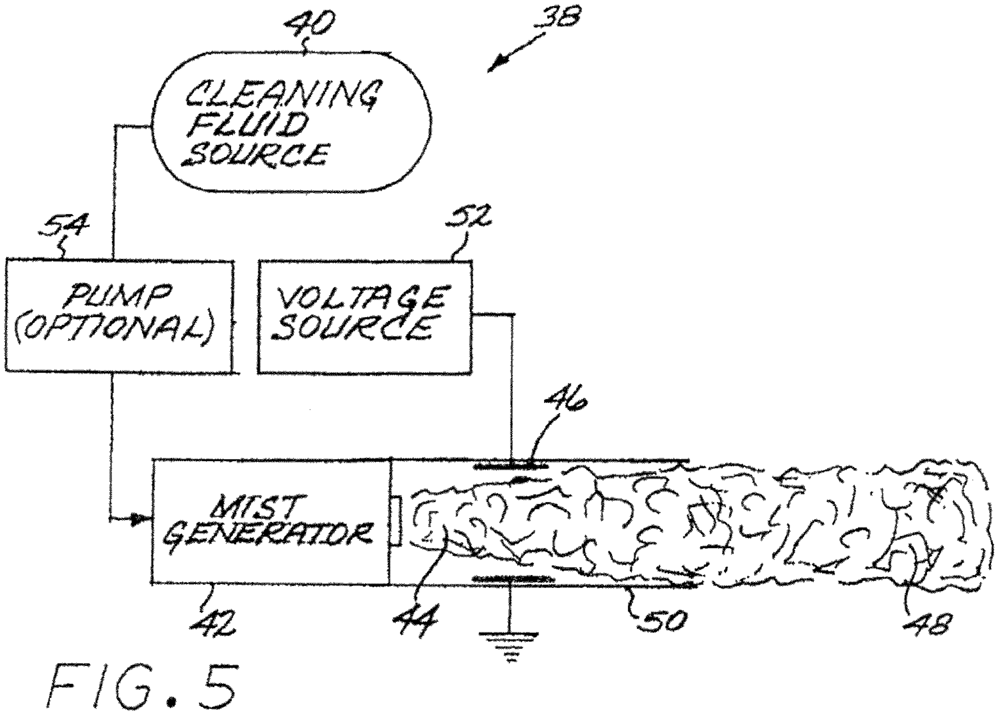
FIG. 5 illustrates a streaming decontamination apparatus.
Figure 8:
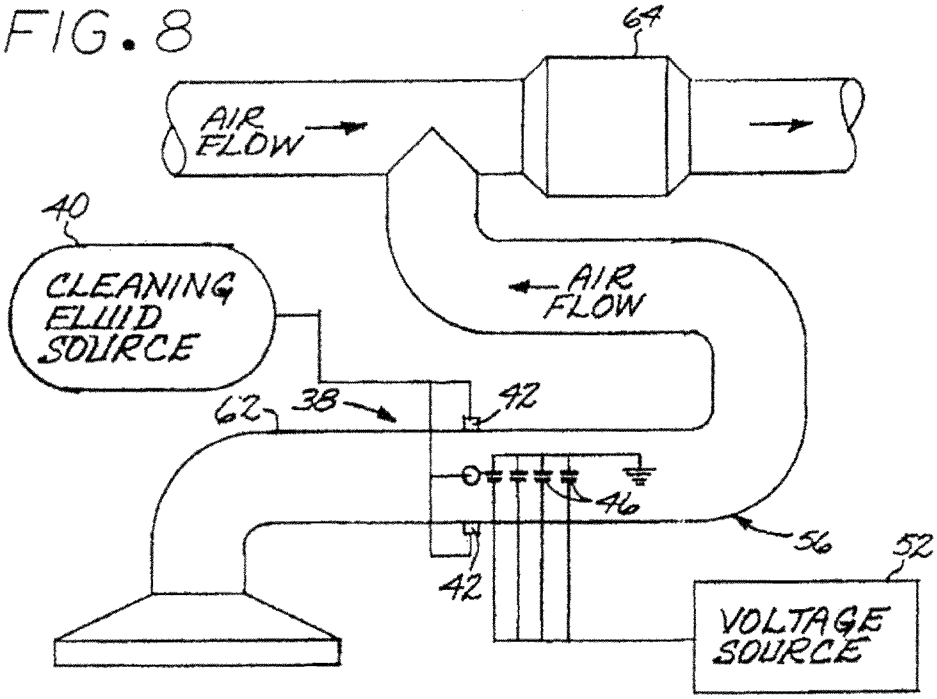
FIG. 8 illustrates a decontamination apparatus for a heating, ventilating, and air conditioning duct system.
Figure 9:
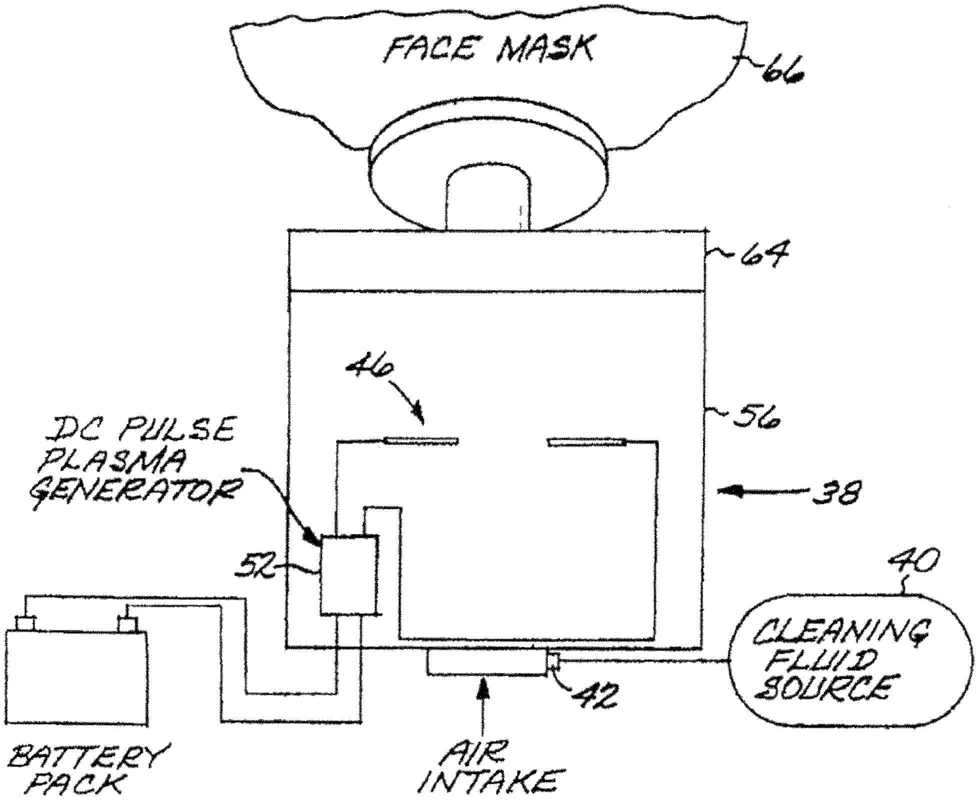
FIG. 9 illustrates a decontamination apparatus for air breathed by a person.
Figure 10A:
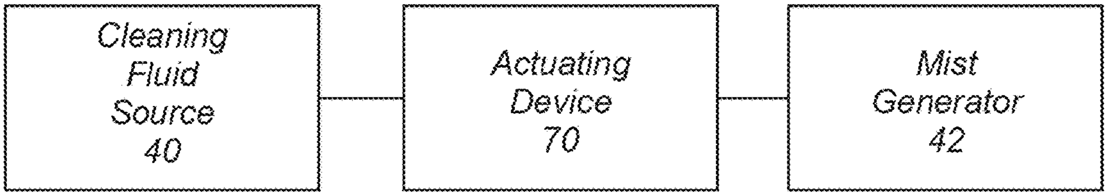
FIG. 10A represents a configuration of device elements wherein a cleaning fluid source 40 and a mist generator 42 are linked via an actuating device 70 that has an adjustable range of rotation of up to 360 degrees.
Figure 10B:
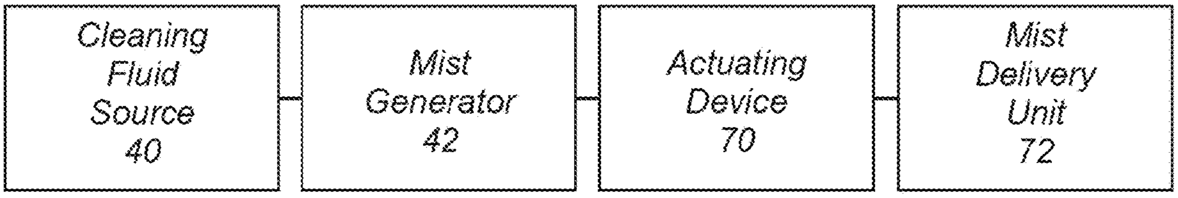
FIG. 10B represents a configuration of device elements wherein a cleaning fluid source 40 is interfaced with a mist generator 42 that, in turn, is linked to a mist delivery unit 72 via an actuating device 70 that has an adjustable range of rotation of up to 360 degrees.
Figure 10C:
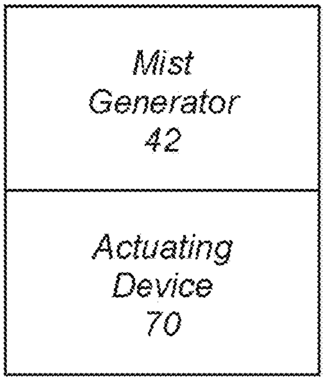
FIG. 10C represents a configuration of device elements wherein a mist generator 42 is mounted on an actuating device 70 that has an adjustable range of rotation of up to 360 degrees.
Figure 10D:
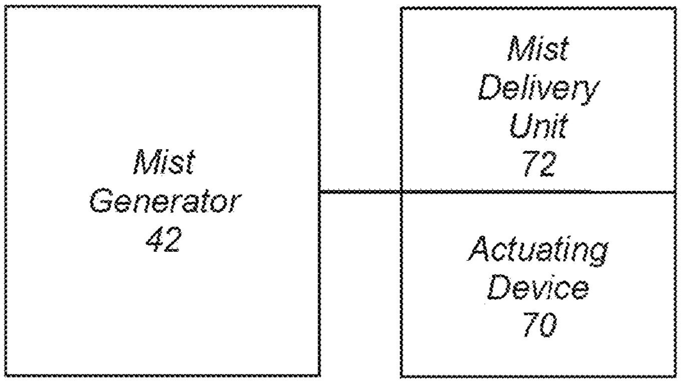
FIG. 10D represents another configuration of device elements wherein a mist generator 42 feeds into a mist delivery unit 72 that is mounted on an actuating device 70 that has an adjustable range of rotation of up to 360 degrees.
Figure 11A:
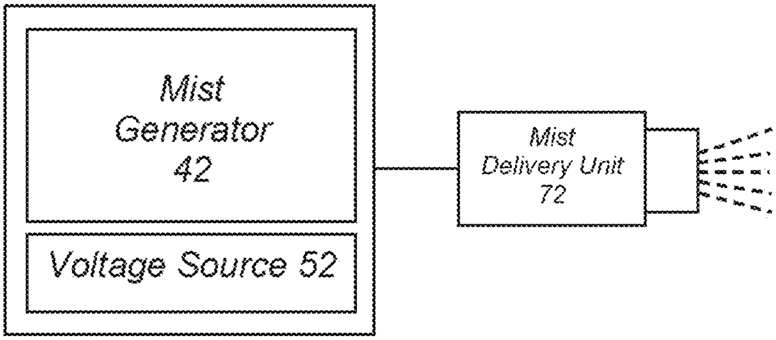
FIG. 11A depicts an embodiment wherein at least a mist generator 42 and a voltage source 52 are contained within a portable housing. The mist generator is functionally connected to a mist delivery unit 72 which may be mounted on the housing or is a remote unit.
Figure 11B:
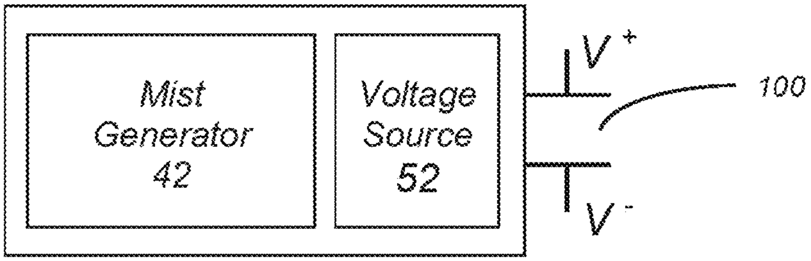
FIG. 11B depicts a mist generator 42 and a voltage source 52 contained within a portable container, wherein the entire unit can be hand held, mounted on another apparatus, or held by/mounted on another machine or a robot.
Figure 11C:
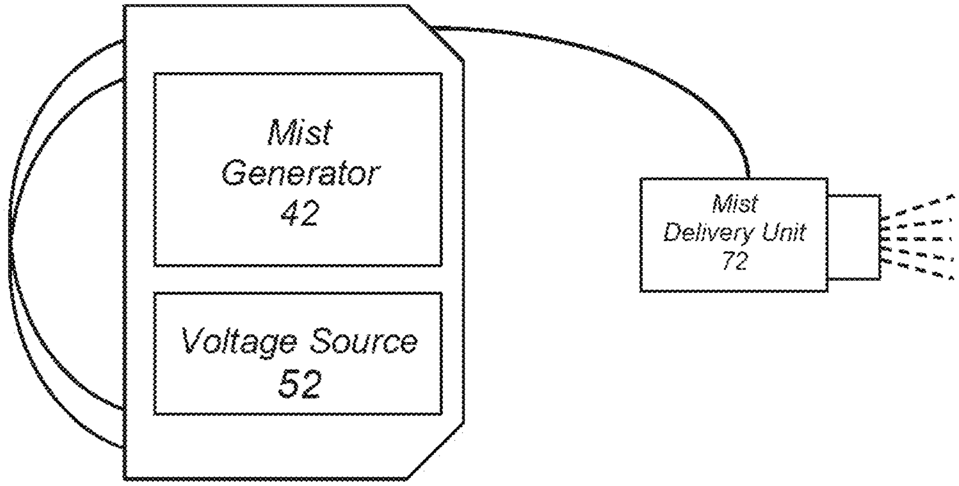
FIG. 11C depicts an exemplary embodiment wherein a mist generator 42 and a voltage source 52 are contained within a wearable container, such as a back pack.
Figure 12A:
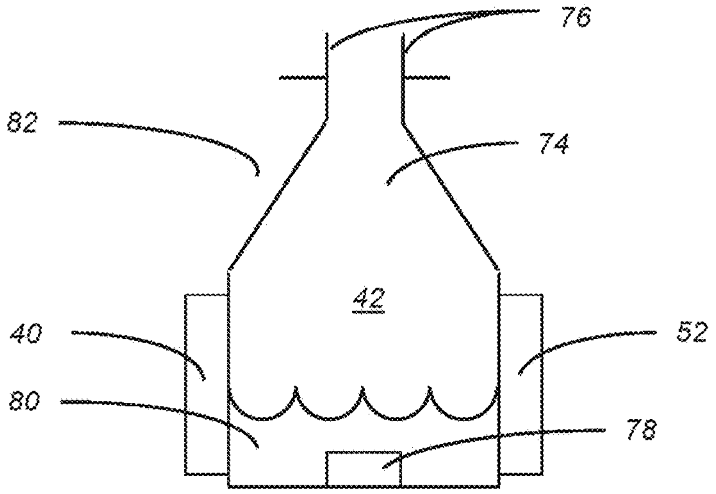
FIG. 12A illustrates the decontamination device comprises an ultrasonic wafer 78 or ultrasonic nebulizer as a mist generator.
Figure 12B:
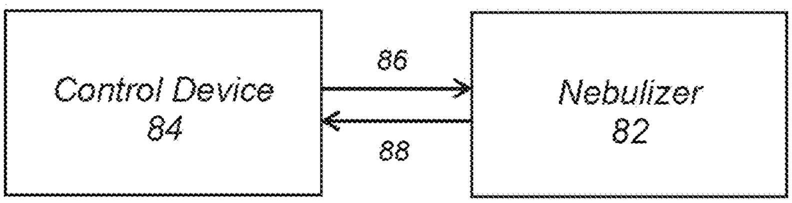
FIG. 12B diagrams a system wherein a mobile/wireless/remote control device 84 is functionally connected to a decontamination device of the present disclosure, such as a nebulizer 82.
Figure 12C:
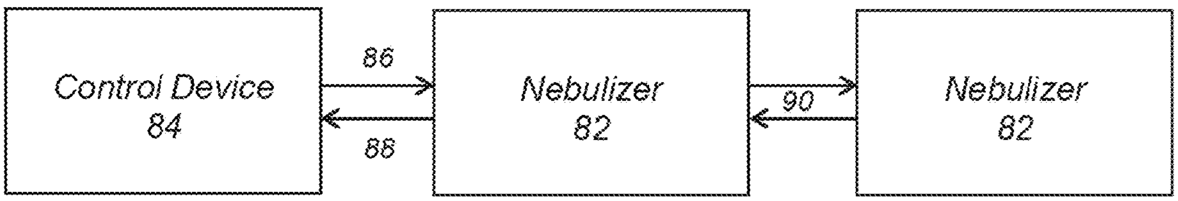
FIG. 12C diagrams an embodiment of the system, wherein the system comprises multiple decontamination devices, such as nebulizers, that are controlled by a control device 84 and further communicate between the nebulizers 82 by wired or wireless means. Information from individual nebulizers 82 can be fed back to the control device 84 either en masse or individually. For example, the dosages emitted by two different nebulizers 82 may start or complete at different times and the data can be reported independently.
Figure 13A:
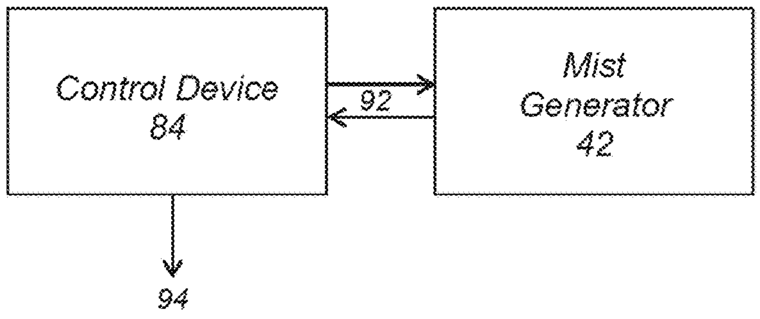
FIGS. 13A-B illustrates a similar system having a single (FIG. 13A) or multiple (FIG. 13B) mist generator(s) 42 being controlled by a control device 84, which further provides data 94 to an external source regarding the treatment of an area or surface.
Figure 13B:
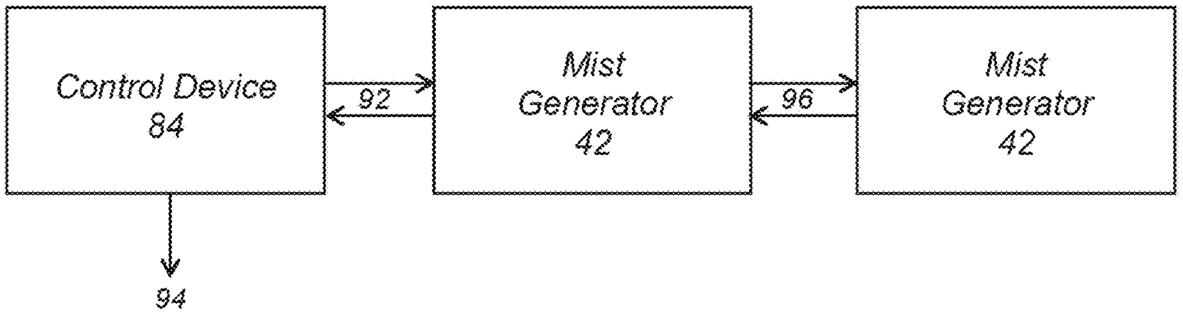
Figure 14:
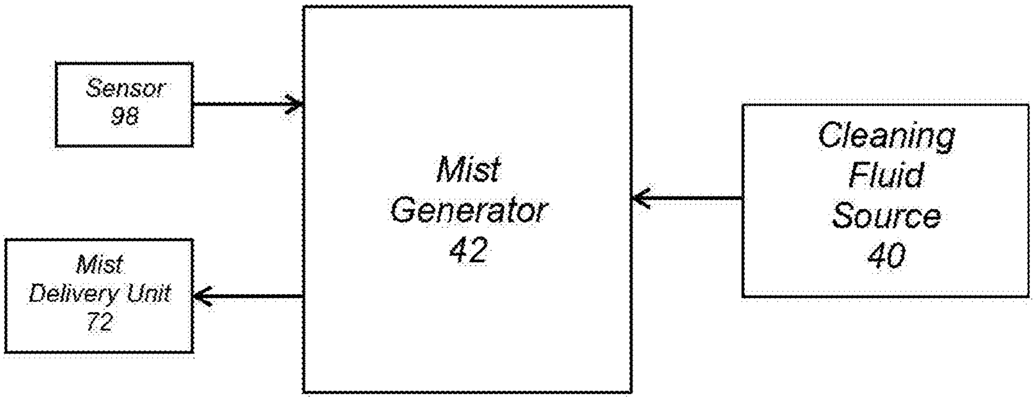
FIG. 14 illustrates a system wherein a mist generator 42, cleaning fluid source 40 and mist delivery unit 72 are further interfaced with a sensor 98.
Figure 15:
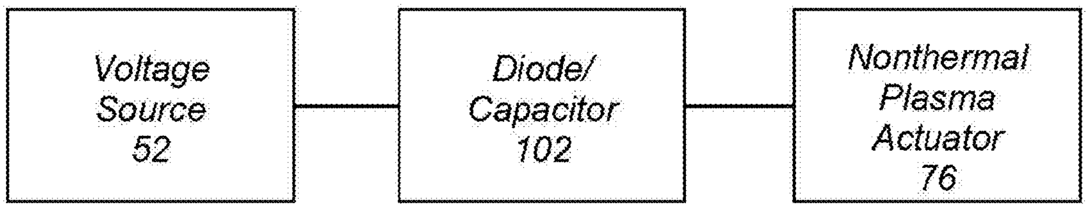
FIG. 15 diagrams an exemplary rectifier for forming free radicals, comprising a voltage source 52, at least one diode/capacitor 102 interfaced with a plasma actuator 76.
Figure 16:
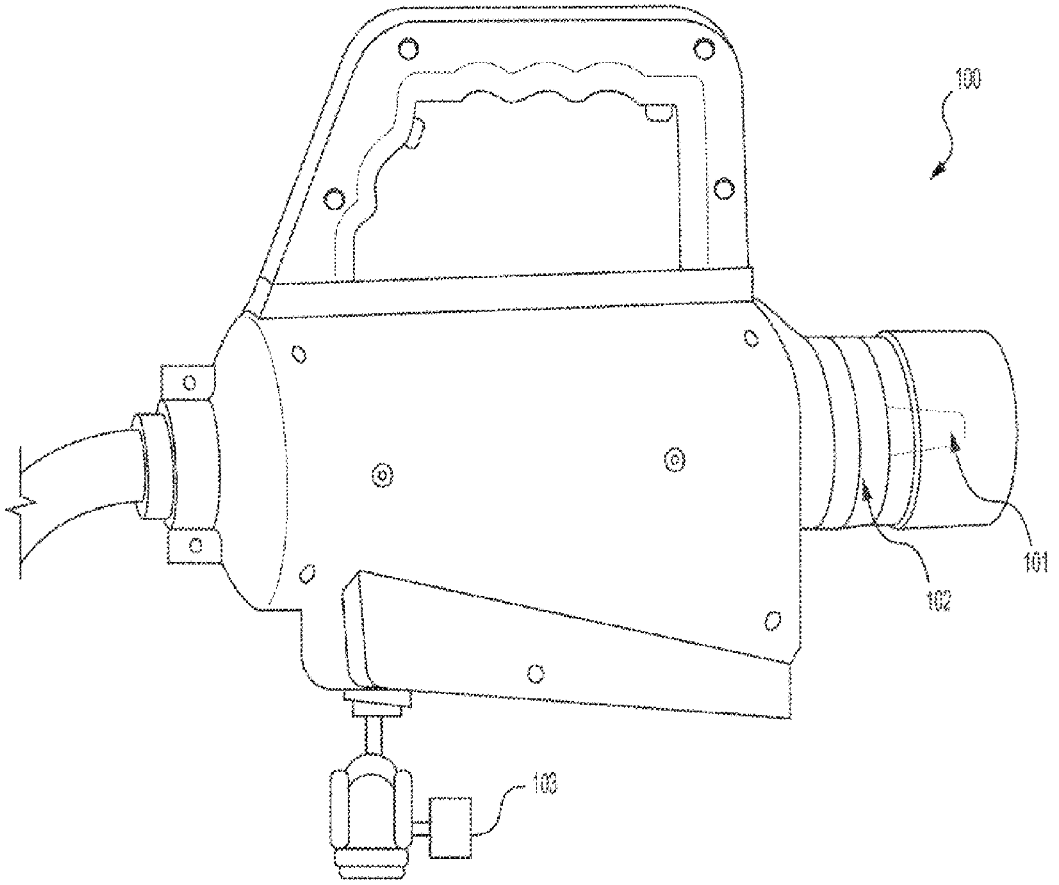
FIG. 16 depicts an embodiment of an ionization/aerosolization and activation device 100 operable manually as a hand-held device and programmable for automated operation.
Figure 17:
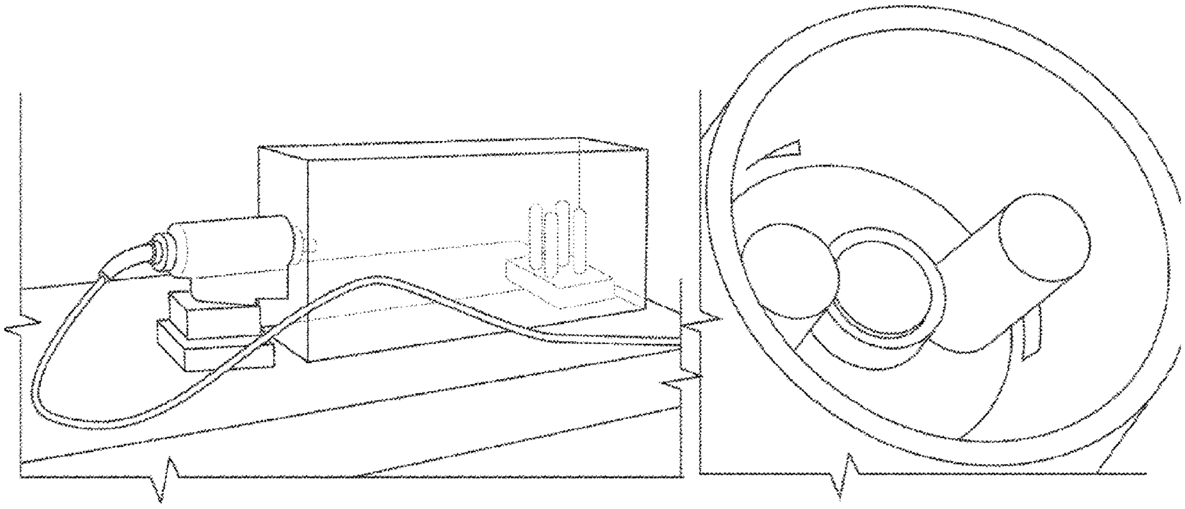
FIG. 17 depicts an embodiment of a display of a programming clock 201 regulating fluid properties of a fluid applied by an ionization/aerosolization and activation device.
Figure 18:
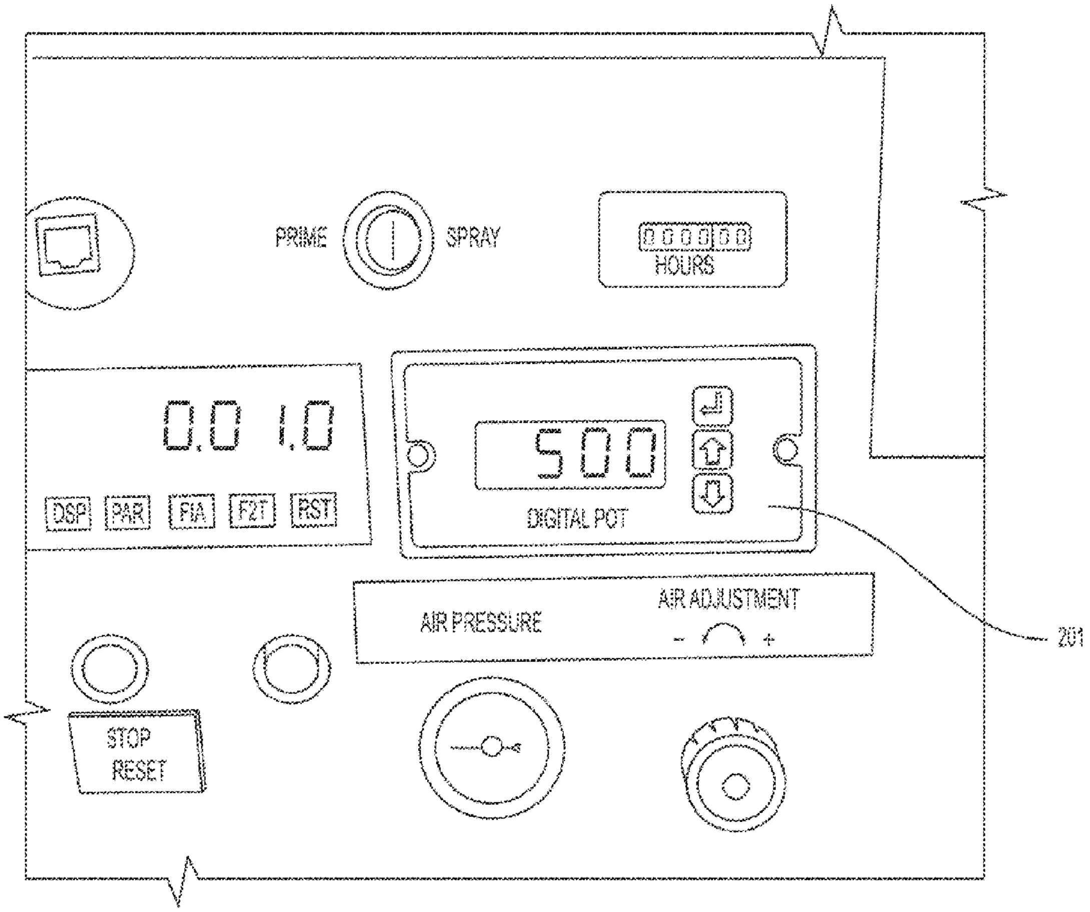
FIG. 18 shows introduction of ionized/aerosolized $H_2O_2$ into a treatment chamber containing tomatoes (left) and close up of the ionization/aerosolization and activation delivering device (right).
Figure 19:
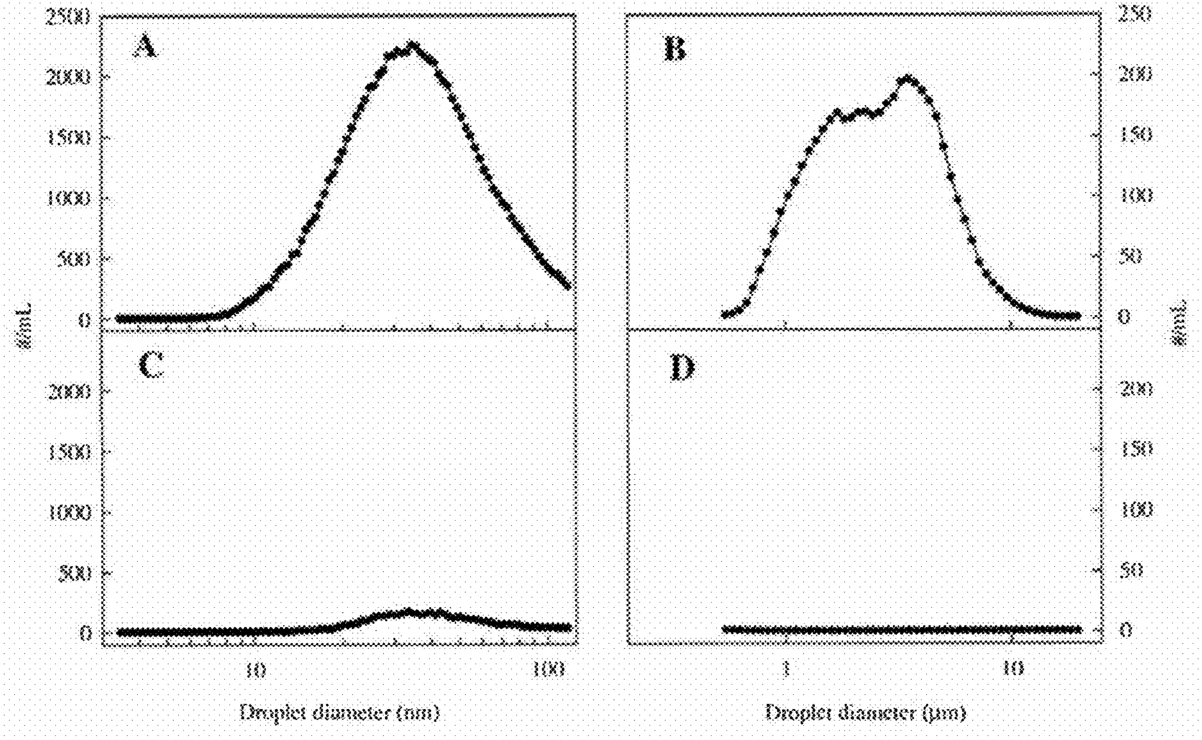
FIG. 19 shows size distribution of droplets in the treatment chamber immediately after the introduction of ionized/aerosolized hydrogen peroxide ($H_2O_2$) and after additional 30 min dwell time.
Figure 20:
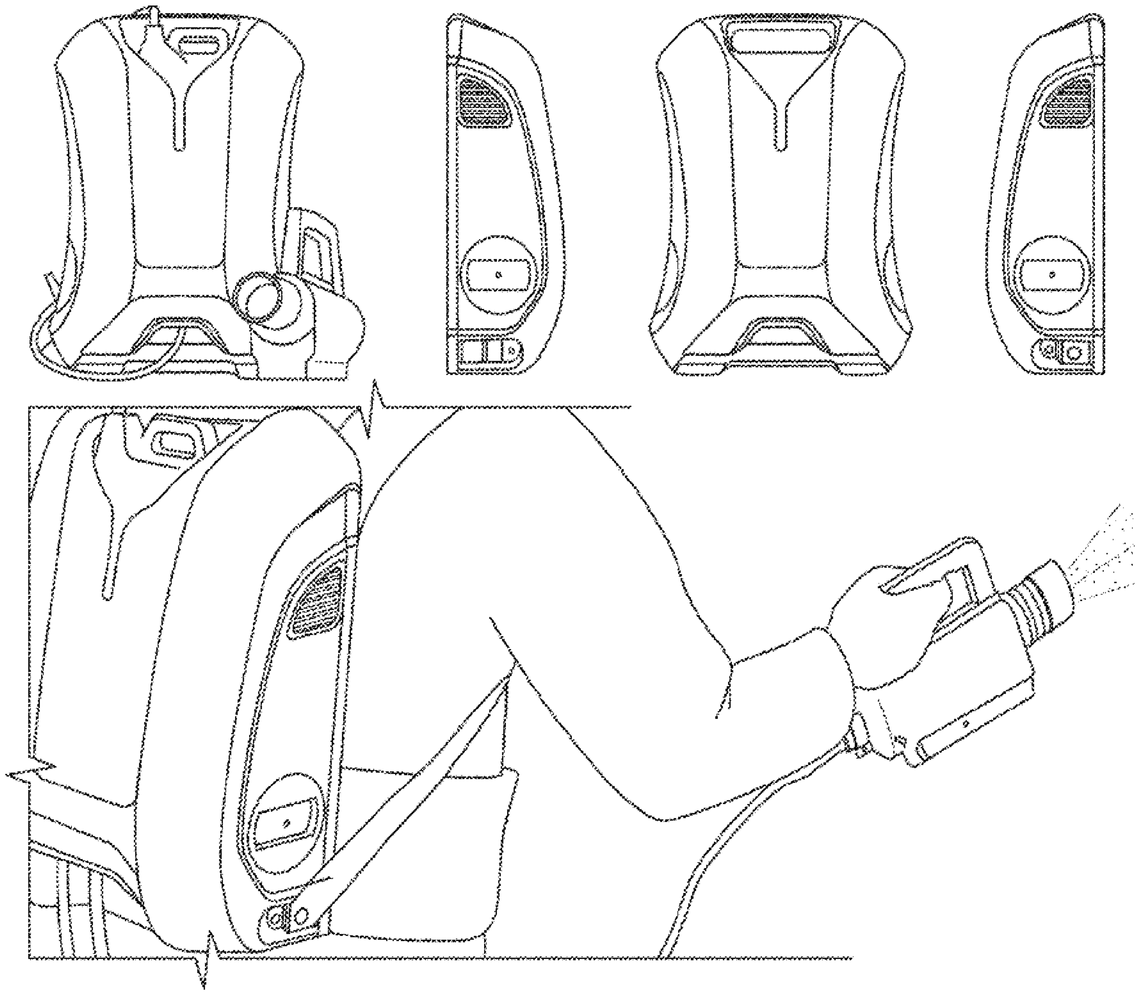
FIG. 20 shows the application of the sterilization system through a backpack.
Figure 21:
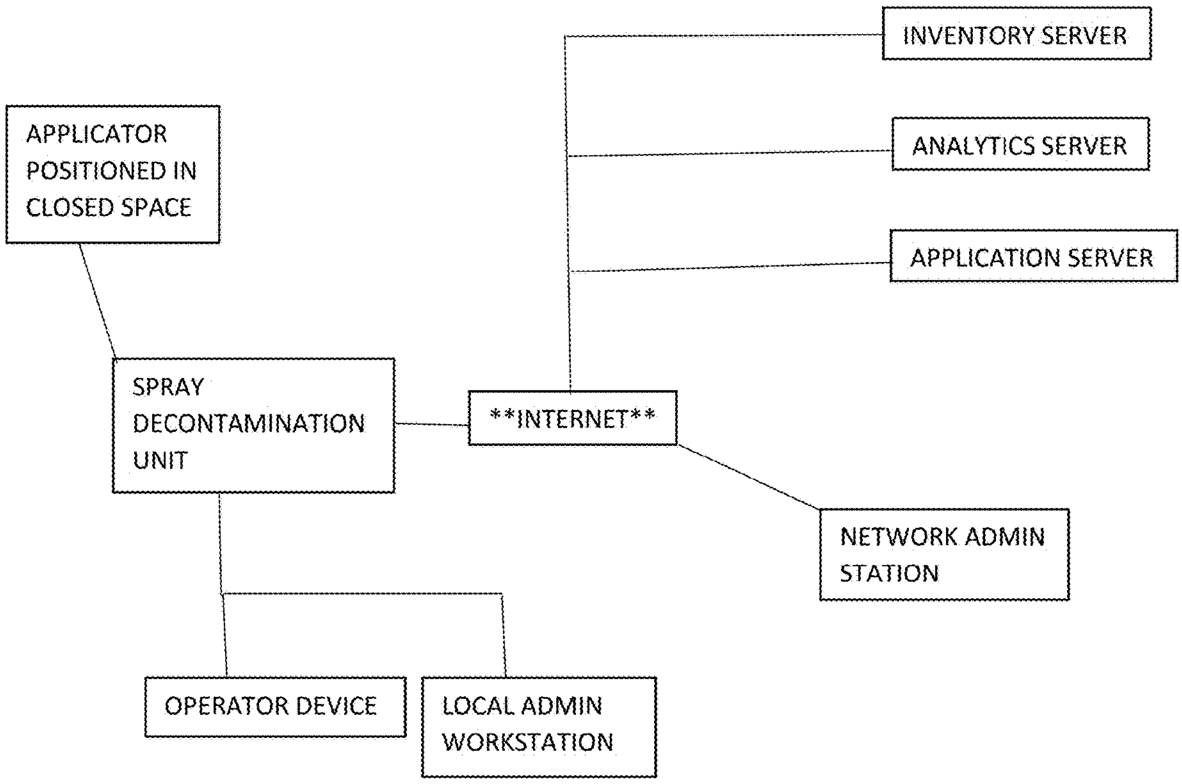
FIG. 21 represents an architecture of the sterilization system components and their relationships.
Figure 22:
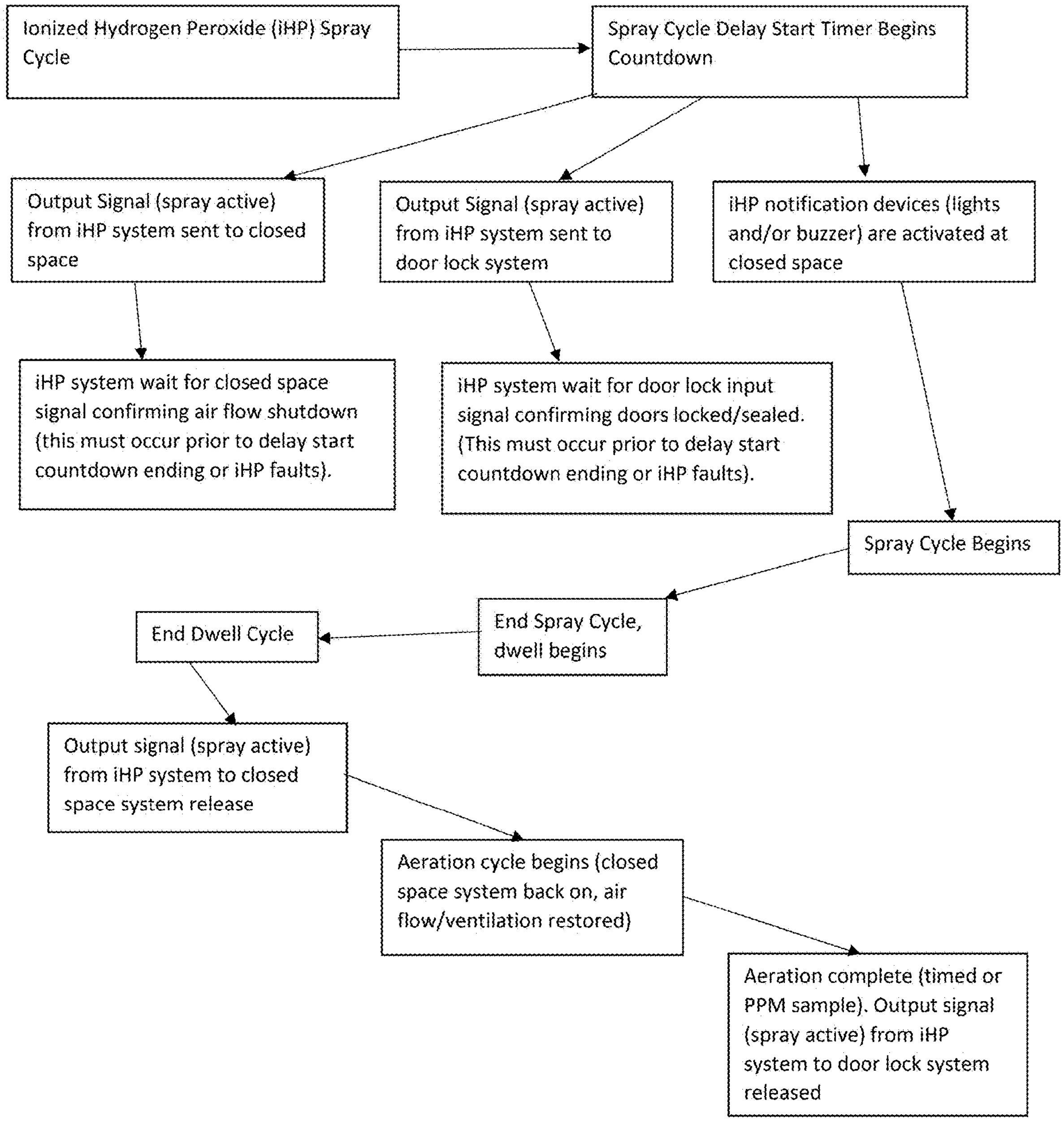
FIG. 22 shows a sterilization systems flow chart.

Throughout the drawings, the same reference numerals and characters, unless otherwise stated are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

The present application describes methods, systems, and means of disinfection through use of automated robotic devices that effectively apply a mist with activated hydroxyl ions in which aerosol droplets will produce an effective high surface area of activated hydroxyl ions. It is an advantage of this approach that no chemical residue is left behind on the disinfected surface, because starting with a small quantity of hydrogen peroxide as a source solution, and then activating hydroxyl ions, means that the dissociated activated species recombine to form diatomic oxygen and water, which are harmless molecules.

Effective disinfection by activated hydroxyl ions as used in the present application depends on the surface area of the droplets that are applied to surfaces; that is the smaller the droplets, the greater the surface area of activated hydroxyl ions on the total cloud of droplets, and thus, the more effective the disinfection method. In fact, soaking a surface for disinfection undermines effectiveness of activated hydroxyl ions because once a surface is soaked the activated ions will not be brought into contact with the bacteria for disinfection.

Activation of the cleaning fluid to produce activated hydroxyl ions may occur through passage of the fluid, for example, an electric arc current, an electromagnetic field, or photonic energy. The fluid may be generated as a spray via, for example, nebulization, ultrasonics, pneumatic spray, or mechanical pressure. However, blowers are not used in the method of the application to generate a spray, as a blower will generate a powerful stream of large droplets that will soak a surface with fluid, which both undermines the impact of any activated hydroxyl ions.

The methods of the application require that a very dry mist (very low diameter aerosol particles as described herein) be generated which carries activated hydroxyl ions through a space to a surface for decontamination. The activated hydroxyl ions make contact with pathogens before recombining to form harmless diatomic oxygen and water (it is an advantage of the approach herein that no chemical residue remains on the disinfected surface). Preferred embodiments of the present application use, for example, a cleaning fluid that comprises 0.3% to 9% hydrogen peroxide as a source of an active species for decontamination of an article or substantially enclosed space. Preferred aerosol droplets that carry activated hydroxyl ions are 0.3-1.0 microns in diameter, with most preferred to average 0.7 microns in diameter. Accordingly, any automated systems applying the present methods require exacting parameters for performance.

The Applicant has improved the efficacy of breaking the double bond of its cleaning solution by redesigning the following aspects. Lowering the electrode posts in the applicator and changing the arc's power source from AC voltage to DC voltage. Lowering the electrode posts puts the arc discharge into a more effective position for activating the cleaning solution prior to dispersion into the treatment area. Changing the arc's power source from AC voltage to DC voltage increases the homogenous charge characteristics of the droplets. This causes a greater percentage of the droplets to repel each other and seek equilibrium. It also increases air ionization, making it easier for the charged droplets to contact surfaces.

Definitions

As used in this specification and the appended claims, the singular forms "a," "an" and "the" include plural referents unless the content clearly dictates otherwise.

As used herein, the term "decontaminating" or "decontamination" means acting to neutralize or remove pathogens from an area or article.

As used herein, the terms "micro-organism" or "pathogen" include, but are not limited to, a bacterium, fungus, yeast, protozoan, virus, or other microorganisms. The term "pathogen" also encompasses targeted bioterror agents.

As used herein, the term "bacteria" shall mean members of a large group of unicellular microorganisms that have cell walls but lack organelles and an organized nucleus. Synonyms for bacteria may include the terms "microorganisms", "microbes", "germs", "bacilli", and "prokaryotes." Exemplary bacteria include, but are not limited to *Mycobacterium* species, including *M. tuberculosis; Staphylococcus* species, including *S. epidermidis, S. aureus*, and methicillin-resistant *S. aureus; Streptococcus* species, including *S. pneumoniae, S. pyogenes, S. mutans, S. agalactiae, S. equi, S. canis, S. bovis, S. equinus, S. anginosus, S. sanguis, S. salivarius, S. mitis*; other pathogenic Streptococcal species, including *Enterococcus* species, such as *E. faecalis* and *E. faecium; Haemophilus influenzae, Pseudomonas* species, including *P. aeruginosa, P. pseudomallei*, and *P. mallei; Salmonella* species, including *S. enterocolitis, S. typhimurium, S. enteritidis, S. bongori*, and *S. choleraesuis; Shigella* species, including *S. flexneri, S. sonnei, S. dysenteriae*, and *S. boydii; Brucella* species, including *B. melitensis, B. suis, B. abortus*, and *B. pertussis; Neisseria* species, including *N. meningitidis* and *N. gonorrhoeae; Escherichia coli*, including enterotoxigenic *E. coli* (ETEC); *Vibrio cholerae, Helicobacter pylori, Geobacillus stearothermophilus, Chlamydia trachomatis, Clostridium difficile, Cryptococcus neoformans, Moraxella* species, including *M. catarrhalis, Campylobacter* species, including *C. jejuni; Corynebacterium* species, including *C. diphtheriae, C. ulcerans, C. pseudotuberculosis, C. pseudodiphtheriticum, C. urealyticum, C. hemolyticum, C. equi; Listeria monocytogenes, Nocardia asteroides, Bacteroides* species, Actinomycetes species, *Treponema pallidum, Leptospirosa species, Klebsiella pneumoniae; Proteus* sp., including *Proteus vulgaris; Serratia* species, *Acinetobacter, Yersinia* species, including *Y. estis* and *Y. pseudotuberculosis; Francisella tularensis, Enterobacter species, Bacteroides species, Legionella species, Borrelia burgdorferi*, and the like. As used herein, the term "targeted bioterror agents" includes, but is not limited to, anthrax (*Bacillus antracis*), plague (*Yersinia pestis*), and tularemia (*Franciscella tularensis*).

As used herein, the term "virus" can include, but is not limited to, influenza viruses, herpesviruses, polioviruses, noroviruses, and retroviruses. Examples of viruses include, but are not limited to, human immunodeficiency virus type 1 and type 2 (HIV-1 and HIV-2), human T-cell lymphotropic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), influenza type A viruses, including subtypes H1N1 and H5N1, human metapneumovirus, severe acute respiratory syndrome (SARS) coronavirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimcan-Congo hemorrhagic fever virus (CCHFV), and hantavirus); Flaviviridae (West Nile virus (WNV), Dengue fever virus (DENV), yellow fever virus (YFV), GB virus C (GBV-C; formerly known as hepatitis G virus (HGV)); Rotaviridae (e.g., rotavirus), and combinations thereof. In one embodiment, the subject is infected with HIV-1 or HIV-2. As used herein, the term "fungi" shall mean any member of the group of saprophytic and parasitic spore-producing eukaryotic typically filamentous organisms formerly classified as plants that lack chlorophyll and include molds, rusts, mildews, smuts, mushrooms, and yeasts. Exemplary fungi include, but are not limited to, *Aspergillus* species, Dermatophytes, *Blastomyces derinatitidis, Candida* species, including *C. albicans* and *C. krusei; Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum, Tinea* species, including *T. versicolor, T. pedis T. unguium, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudanense, T. equinum, T. crinacei*, and *T. verrucosum; Mycoplasma genitalia; Microsporum* species, including *M. audouini, M. ferrugineum, M. canis, M. nanum, M. distortum, M. gypseum, M. fulvum*, and the like.

"Enveloped viruses" are usually inactivated by effective surface cleaning and disinfection. Enveloped viruses possess an envelope composed of a lipid layer (fat-like substance that is water insoluble) that forms an outer coating. The virus envelope is required for attachment of the virus to a target cell. The lipid layers in cellular membranes are impermeable to most polar or charged solutes but are permeable to apolar compounds, such as the lipids making up a viral envelope. Individual enveloped viruses have differing modes of transmission; however, typical routes of transmission are via indirect or direct bodily contact with infectious virus particles, such as by inhalation or contact with respiratory droplets carrying a viral load. Viruses can persist on surfaces for prolonged periods of time and still be infectious, therefore there is a need to decontaminate such surfaces.

"Coronaviruses" are enveloped viruses with a positive-sense single-stranded RNA genome and a nucleocapsid of helical symmetry. Coronavirus virions are generally considered to have on average diameters of 80-120 nm, but the size range can vary from 50 nm up to 200 nm. Characteristic surface spikes or peplomers, which appear club-like, pear-shaped, or petal-shaped, project some 17-20 nm from the virion surface, having a thin base that swells to a width of about 10 nm at the distal extremity. In certain coronaviruses a second set of projections, 5-10 nm long, forms an undergrowth beneath the major spikes.

Coronavirus infections begin with the binding of virions to host cellular receptors. The infection culminates in the deposition of the nucleocapsid into the cytoplasm, where the viral genome becomes available for translation. The positive sense genome, which functions in effect as the first mRNA of viral infection, is translated into the enormous replicase polyprotein. The replicase then uses the genome as the template for the synthesis, via negative strand intermediates, of both new viral genomes and a set of subgenomic mRNAs. The latter are translated into structural proteins and accessory proteins. The membrane-bound structural proteins, M, S, and E, are inserted into the ER, from where they transit to the endoplasmic reticulum-Golgi intermediate compartment (ERGIC). Nucleocapsids are formed from the encapsidation of progeny genomes by N protein, and these coalesce with the membrane-bound components, forming virions by budding into the ERGIC. Finally, progeny virions are exported from infected cells by transport to the plasma membrane in smooth-walled vesicles, or Golgi sacs, that remain to be more clearly defined. During infection by some coronaviruses, but not others, a fraction of S protein that has not been assembled into virions ultimately reaches the plasma membrane. At the cell surface S protein can cause the fusion of an infected cell with adjacent, uninfected cells, leading to the formation of large, multinucleate syncytia. This enables the spread of infection independent of the action of extracellular virus, thereby providing some measure of escape from immune surveillance.

In certain embodiments, the methods and compositions of the present application are used to decontaminate environments potentially infected by any coronavirus in the Orthocoronavirinae family, including but not limited to those described herein. The genetically diverse Orthocoronavirinae family is divided into four genera (alpha, beta, gamma, and delta coronaviruses). Human CoVs are limited to the alpha and beta subgroups. Exemplary human CoVs include severe acute respiratory syndrome coronavirus-2 (SARS-CoV-2), severe acute respiratory syndrome coronavirus (SARS-CoV), Middle East respiratory syndrome coronavirus (MERS-CoV), HCoV-229E, HCoV-OC43, HCoV-NL63, and HCoV-HKU1.

Zoonotic CoVs have a natural predilection for emergence into new host species giving rise to new diseases most recently exemplified in humans by severe acute respiratory syndrome coronavirus 2 (SARS-CoV-2), severe acute respiratory syndrome coronavirus (SARS-CoV), and Middle East respiratory syndrome coronavirus (MERS-CoV) (de Wit et al., 2016). Interestingly, all known human CoVs are thought to have emerged as zoonoses from wild or domestic animals.

Nonlimiting examples of subgroup 1a alphacoronaviruses and their GenBank Accession Nos. include FCov.FIPV.79.1146. VR.2202 (NV_007025), transmissible gastroenteritis virus (TGEV) (NC_002306; Q811789.2; DQ811786.2; DQ811788.1; DQ811785.1; X52157.1; AJ011482.1; KC962433.1; AJ271965.2; JQ693060.1; KC609371.1; JQ693060.1; JQ693059.1; JQ693058.1; JQ693057.1; JQ693052.1; JQ693051.1; JQ693050.1); porcine reproductive and respiratory syndrome virus (PRRSV) (NC_001961.1; DQ811787), as well as any subtype, clade or sub-clade thereof, including any other subgroup 1a coronavirus now known (e.g., as can be found in the GenBank® Database) or later identified in the GenBank® Database.

Nonlimiting examples of a subgroup 1b alphacoronaviruses and their GenBank Accession Nos. include HCoV.NL63.Amsterdam.I (NC_005831), BtCoV.HKU2.HK.298.2006 (EF203066), BtCoV.HKU2.HK.33.2006 (EF203067), BtCoV.HKU2.HK.46.2006 (EF203065), BtCoV.HKU2.GD.430.2006 (EF203064), BtCoV.1A.AFCD62 (NC_010437), BtCoV.1B.AFCD307 (NC_010436), BtCov.HKU8.AFCD77 (NC_010438), BtCoV.512.2005 (DQ648858); porcine epidemic diarrhea viruses (NC_003436, DQ355224.1, DQ355223.1, DQ355221.1, JN601062.1, JN601061.1, JN601060.1, JN601059.1, JN601058.1, JN601057.1, JN601056.1, JN601055.1, JN601054.1, JN601053.1, JN601052.1, JN400902.1, JN547395.1, FJ687473.1, FJ687472.1, FJ687471.1, FJ687470.1, FJ687469.1, FJ687468.1, FJ687467.1, FJ687466.1, FJ687465.1, FJ687464.1, FJ687463.1, FJ687462.1, FJ687461.1, FJ687460.1, FJ687459.1, FJ687458.1, FJ687457.1, FJ687456.1, FJ687455.1, FJ687454.1, FJ687453 FJ687452.1, FJ687451.1, FJ687450.1, FJ687449.1, AF500215.1, KF476061.1, KF476060.1, KF476059.1, KF476058.1, KF476057.1, KF476056.1, KF476055.1, KF476054.1, KF476053.1, KF476052.1, KF476051.1, KF476050.1, KF476049.1, KF476048.1, KF177258.1, KF177257.1, KF177256.1, KF177255.1), HCoV.229E (NC_002645), as well as any subtype, clade or sub-clade thereof, including any other subgroup 1b coronavirus now known (e.g., as can be found in the GenBank® Database) or later identified in the GenBank® Database.

Nonlimiting examples of subgroup 2a betacoronaviruses and their GenBank Accession Nos. include HCoV.HKU1.C.N5 (DQ339101), MHV.A59 (NC_001846), PHEV.VW572 (NC_007732), HCoV.OC43.ATCC.VR.759 (NC_005147), bovine enteric coronavirus (BCoV.ENT) (NC_003045), as well as any subtype, clade or sub-clade thereof, including any other subgroup 2a coronavirus now known (e.g., as can be found in the GenBank® Database) or later identified in the GenBank® Database.

Nonlimiting examples of subgroup 2b betacoronaviruses and their GenBank Accession Nos. include human SARS CoV-2 isolates, such as Wuhan-Hu-1 (NC_045512.2) and any CoV-2 isolates comprising a genomic sequence set forth in GenBank Accession Nos., such as MT079851.1, MT470137.1, MT121215.1, MT438728.1, MT470115.1, MT358641.1, MT449678.1, MT438742.1, LC529905.1, MT438756.1, MT438751.1, MT460090.1, MT449643.1, MT385425.1, MT019529.1, MT449638.1, MT374105.1, MT449644.1, MT385421.1, MT365031.1, MT385424.1, MT334529.1, MT466071.1, MT461669.1, MT449639.1, MT415321.1, MT385430.1, MT135041.1, MT470179.1, MT470167.1, MT470143.1, MT365029.1, MT114413.1, MT192772.1, MT135043.1, MT049951.1; human SARS CoV-1 isolates, such as SARS CoV.A022 (AY686863), SARSCoV.CUHK-W1 (AY278554), SARSCoV.GD01 (AY278489), SARSCoV.HC.SZ.61.03 (AY515512), SARS-CoV.SZ16 (AY304488), SARSCoV.Urbani (AY278741), SARSCoV.civet010 (AY572035), SARSCoV.MA.15 (DQ497008); bat SARS CoV isolates, such as BtSARS.HKU3.1 (DQ022305), BtSARS.HKU3.2 (DQ084199), BtSARS.HKU3.3 (DQ084200), BtSARS.Rml (DQ412043), BtCoV.279.2005 (DQ648857), BtSARS.Rf1 (DQ412042), BtCoV.273.2005 (DQ648856), BtSARS.Rp3 (DQ071615), as well as any subtype, clade or sub-clade thereof, including any other subgroup 2b coronavirus now known (e.g., as can be found in the GenBank® Database) or later identified in the GenBank® Database.

Nonlimiting examples of subgroup 2c betacoronaviruses and their GenBank Accession Nos. include Middle East respiratory syndrome coronavirus (MERS) isolates, such as Riyadh 22012 (KF600652.1), Al-Hasa_18_2013 (KF600651.1), Al-Hasa_17_2013 (KF600647.1), Al-Hasa_152013 (KF600645.1), Al-Hasa_16_2013 (KF600644.1), Al-Hasa_21_2013 (KF600634), Al-Hasa 19_2013 (KF600632), Buraidah_1_2013 (KF600630.1), Hafr-Al-Batin_1_2013 (KF600628.1), Al-Hasa_122013 (KF600627.1), Bisha.ltoreq.1_2012 (KF600620.1), Riyadh_3_2013 (KF600613.1), Riyadh_1_2012

(KF600612.1), Al-Hasa_3_2013 (KF186565.1), Al-Hasa_1_2013 (KF186567.1), Al-Hasa_2_2013 (KF186566.1), Al-Hasa_4_2013 (KF186564.1); Betacoronavirus England 1-N1 (NC_019843), SA-N1 (KC667074); human betacoronavirus 2c Jordan-N3/2012 (KC776174.1); human betacoronavirus 2c EMC/2012, (JX869059.2); any bat coronavirus subgroup 2c isolate, such as bat coronavirus Taper/CII_KSA_287/Bisha/Saudi Arabia (KF493885.1), bat coronavirus Rhhar/CII_KSA 003/Bisha/Saudi Arabia/2013 (KF493888.1), bat coronavirus Pikuh/CII_KSA_001/Riyadh/Saudi Arabia/2013 (KF493887.1), bat coronavirus Rhhar/CII_KSA 002/Bisha/Saudi Arabia/2013 (KF493886.1), bat coronavirus Rhhar/CII_KSA_004/Bisha/Saudi Arabia/2013 (KF493884.1), bat coronavirus BtCoV.HKU4.2 (EF065506), bat coronavirus BtCoV.HKU4.1 (NC_009019), bat coronavirus BtCoV.HKU4.3 (EF065507), bat coronavirus BtCoV.HKU4.4 (EF065508), bat coronavirus BtCoV133.2005 (NC_008315), bat coronavirus BtCoV.HKU5.5 (EF065512), bat coronavirus BtCoV.HKU5.1 (NC_009020), bat coronavirus BtCoV.HKU5.2 (EF065510), bat coronavirus BtCoV.HKU5.3 (EF065511), and bat coronavirus HKU5 isolate (KC522089.1); any additional subgroup 2c, such as KF192507.1, KF600656.1, KF600655.1, KF600654.1, KF600649.1, KF600648.1, KF600646.1, KF600643.1, KF600642.1, KF600640.1, KF600639.1, KF600638.1, KF600637.1, KF600636.1, KF600635.1, KF600631.1, KF600626.1, KF600625.1, KF600624.1, KF600623.1, KF600622.1, KF600621.1, KF600619.1, KF600618.1, KF600616.1, KF600615.1, KF600614.1, KF600641.1, KF600633.1, KF600629.1, KF600617.1, KC869678.2; KC522088.1, KC522087.1, KC522086.1, KC522085.1, KC522084.1, KC522083.1, KC522082.1, KC522081.1, KC522080.1, KC522079.1, KC522078.1, KC522077.1, KC522076.1, KC522075.1, KC522104.1, KC522104.1, KC522103.1, KC522102.1, KC522101.1, KC522100.1, KC522099.1, KC522098.1, KC522097.1, KC522096.1, KC522095.1, KC522094.1, KC522093.1, KC522092.1, KC522091.1, KC522090.1, KC522119.1, KC522118.1, KC522117.1, KC522116.1, KC522115.1, KC522114.1, KC522113.1, KC522112.1, KC522111.1, KC522110.1, KC522109.1, KC522108.1, KC522107.1, KC522106.1, KC522105.1); *Pipistrellus* bat coronavirus HKU4 isolates (KC522048.1, KC522047.1, KC522046, 1, KC522045.1, KC522044.1, KC522043.1, KC522042.1, KC522041.1, KC522040.1, KC522039.1, KC522038.1, KC522037.1, KC522036.1, KC522048.1, KC522047.1, KC522046.1, KC522045.1, KC522044.1, KC522043.1, KC522042.1, KC522041.1, KC522040, 1, KC522039.1, KC522038.1, KC522037.1, KC522036.1, KC522061.1, KC522060.1, KC522059.1, KC522058.1, KC522057.1, KC522056.1, KC522055.1, KC522054.1, KC522053.1, KC522052.1, KC522051.1, KC522050.1, KC522049.1, KC522074.1, KC522073.1, KC522072.1, KC522071.1, KC522070.1, KC522069.1, KC522068.1, KC522067.1, KC522066.1, KC522065.1, KC522064.1, KC522063.1, KC522062.1), as well as any subtype, clade or sub-clade thereof, including any other subgroup 2c coronavirus now known (e.g., as can be found in the GenBank® Database) or later identified in the GenBank® Database.

Nonlimiting examples of subgroup 2d betacoronaviruses and their GenBank Accession Nos. include BtCoV.HKU9.2 (EF065514), BtCoV.HKU9.1 (NC_009021), BtCoV.HKU9.3 (EF065515), BtCoV.HKU9.4 (EF065516), as well as any subtype, clade or sub-clade thereof, including any other subgroup 2d coronavirus now known (e.g., as can be found in the GenBank® Database) or later identified in the GenBank® Database.

Nonlimiting examples of subgroup 3 gamma coronaviruses include IBV.Beaudette.IBV.p65 (DQ001339) or any other subgroup 3 coronavirus now known (e.g., as can be found in the GenBank® Database) or later identified in the GenBank® Database.

A coronavirus defined by any of the isolates or genomic sequences in the aforementioned subgroups 1a, 1b, 2a, 2b, 2c, 2d and 3 can be targeted for decontamination in accordance with the methods and compositions of the present application.

Coronaviruses have widely been known to cause respiratory and intestinal infections in humans after the outbreak of "severe acute respiratory syndrome (SARS)." SARS was caused by SARS-CoV, and was followed by "Middle East respiratory syndrome (MERS)" caused by MERS-CoV. The outbreak of COVID-19 is caused by a coronavirus named SARS-CoV-2 (due to its similarity to SARS-CoV). SARS-CoV infects ciliated bronchial epithelial cells and type-II pneumocytes through angiotensin-converting enzyme 2 (ACE2) as receptor; mechanism of action for SARS-CoV-2 are still being determined.

It has been estimated the environmental stability of SARS-CoV-2 is up to three hours in the air post-aerosolisation, up to four hours on copper, up to 24 hours on cardboard and up to two to three days on plastic and stainless steel. These findings are similar to results obtained for environmental stability of SARS-CoV-1.

SARS-CoV-2 has been detected in environmental samples from COVID-19 dedicated intensive care units (ICU) in hospitals. In rooms of COVID-19 patients, different levels of environmental contamination have been detected, ranging from 1 out of 13 to 13 out of 15 samples testing positive for SARS-CoV-2 prior to cleaning. One sample from an air exhaust outlet was positive indicating that virus particles may be displaced by air and deposited on surfaces, although no direct air samples tested positive. SARS-CoV-2 was also detected on objects such as the self-service printers used by patients to self-print the results of their exams, desktop keyboards and doorknobs. Virus was detected most commonly on gloves and, even rarely, on eye protection. The evidence shows the threat of contamination of SARS-CoV-2 in the environment of a COVID-19 patient, therefore reinforcing the need for decontamination of these environments. The decontamination methods described herein provide an effective solution.

As used herein, the term "protozoan" shall mean any member of a diverse group of eukaryotes that are primarily unicellular, existing singly or aggregating into colonies, are usually nonphotosynthetic, and are often classified further into phyla according to their capacity for and means of motility, as by pseudopods, flagella, or cilia. Exemplary protozoans include, but are not limited to *Plasmodium* species, including *P. falciparum, P. vivax, P. ovale*, and *P. malariae; Leishmania* species, including *L. major, L. tropica, L. donovani, L. infantum, L. chagasi, L. mexicana, L. panamensis, L. braziliensis* and *L. guyanensi; Cryptosporidium, Isospora belli, Toxoplasma gondii, Trichomonas vaginalis*, and *Cyclospora* species.

As used herein, the term "article" means any solid item or object that may be susceptible to contamination with pathogens. As used herein, the term "substantially enclosed space" means a room, a tent, a building, or any man-made structure that is substantially enclosed and may be susceptible to contamination with pathogens. The term "substantially enclosed space" is not limited to man-made structures (e.g., caves or natural tunnels are also substantially enclosed spaces), even though embodiments illustrated herein may be preferably directed to decontamination of such structures As used herein, the term "sensor" can refer to any type of sensor suitable for detecting contamination on an apparatus, a surface, or in a substantially enclosed space. Examples of sensors include, but are not limited to, photosensors, voltaic sensors, weight sensors, moisture sensors, pressure sensors, or any type of biosensor.

As used herein, an "enclosed space" refers to any chamber, container or space that can be decontaminated with the system of the present disclosure. Examples of enclosed spaces include, but are not limited to, any chamber used in everyday to conduct highly controlled research projects/spaces, sanitation chambers (such as gynoprobe cabinets), biosafety cabinets, glovebox, research hoods and clinical spaces.

As used herein, a "computer" may be either a general-purpose computer or a specialized device built to solely carry out one or more specific purposes.

As used herein, an "applicator" may be any form of device that can carry out a decontamination process. In particular embodiments, applicators apply decontamination processes by spray misting a substantially enclosed space.

As used herein, the term "article" means any solid item or object that may be susceptible to contamination with pathogens. As used herein, the term "substantially enclosed space" means a room, a tent, a building, or any man-made structure that is substantially enclosed and may be susceptible to contamination with pathogens. The term "substantially enclosed space" is not limited to man-made structures, even though embodiments illustrated herein may be preferably directed to decontamination of such structures.

As used herein, the term "sensor" can refer to any type of sensor suitable for detecting contamination on an apparatus, a surface, or in a substantially closed space. Examples of sensors include, but are not limited to, photosensors, voltaic sensors, weight sensors, moisture sensors, pressure sensors, or any type of biosensor.

As used herein, the term "shearing" refers to the process of using force to fragment liquid particles into discrete groups that move and flow as energized independent subgroups of sheared particles until the groups of particles transition in fluid phase into a mist. As used herein, the term "mist" means a cloud of aerosol droplets. As used herein, the term "aerosol" is a colloid of fine liquid droplets of about 1 to about 20 micrometers in diameter.

As used herein, the term "cleaning fluid" or "decontamination fluid" refers to the source of an active species used to decontaminate an article or substantially enclosed space. The preferred active species is hydroxyl ions, and the preferred source is hydrogen peroxide. The source may instead be a more-complex species that produces hydroxyl ions upon reaction or decomposition. Examples of such more-complex species include peracetic acid (CH2COO—OH+H2O), sodium percarbonate (2Na2CO3+3H2O2), and gluteraldehyde (CH8O2). The cleaning fluid may further include promoting species that aid the active species in accomplishing its attack upon the biological microorganisms. Examples of such promoting species include ethylenediaminetetraacetate, isopropyl alcohol, enzymes, fatty acids, and acids. The cleaning fluid is of any operable type. The cleaning fluid must contain an activatable species. A preferred cleaning fluid comprises a source of hydroxyl ions (OH—) for subsequent activation. Such a source may be hydrogen peroxide (H2O2) or a precursor species that produces hydroxyl ions. Other sources of hydroxyl ions may be used as appropriate. Examples of other operable sources of hydroxyl ions include peracetic acid (CH2COO—OH+H2O), sodium percarbonate (2Na2CO3+3H2O2), and gluteraldehyde (CH8O2). Other activatable species and sources of such other activatable species may also be used.

The cleaning fluid may also contain promoting species that are not themselves sources of activatable species such as hydroxyl ions, but instead modify the decontamination reactions in some beneficial fashion. Examples include ethylenediaminetetraacetate (EDTA), which binds metal ions and allows the activated species to destroy the cell walls more readily; an alcohol such as isopropyl alcohol, which improves wetting of the mist to the cells; enzymes, which speed up or intensity the redox reaction in which the activated species attacks the cell walls; fatty acids, which act as an ancillary anti-microbial and may combine with free radicals to create residual anti-microbial activity; and acids such as citric acid, lactic acid, or oxalic acid, which speed up or intensity the redox reaction and may act as ancillary anti-microbial species to pH-sensitive organisms. Mixtures of the various activatable species and the various promoting species may be used as well. The cleaning fluids are preferably aqueous solutions, but may be solutions in organics such as alcohol. The cleaning fluid source may be a source of the cleaning fluid itself, or a source of a cleaning fluid precursor that chemically reacts or decomposes to produce the cleaning fluid.

As used herein, the term "a nonthermal plasma actuator" or "applicator" means an actuator that activates the cleaning fluid to an activated condition such as the ionized, plasma, or free radical states which, with the passage of time, returns to the non-activated state (a process termed "recombination"). To accomplish the activation, the activator produces activating energy such as electric energy or photonic energy. The photonic energy may be produced by a laser. Examples of activators include an AC electric field, an AC arc, a DC electric field, a pulsed DC electric field, a DC arc, an electron beam, an ion beam, a microwave beam, a radio frequency beam, and an ultraviolet light beam. The activator may include a tuner that tunes the amplitude, frequency, wave form, or other characteristic of the activating energy to achieve a desired, usually a maximum, re-combination time of the activated cleaning fluid mist. As used herein, the term "plasma activated ionic particles" means activated OH-ions.

An aspect of the application relates to a multi-configuration system for decontamination, comprising: one or more sensors, one or more applicators and a system controller, wherein when the one or more sensors detect the presence of a micro-organism, the system controller orders the one or more applicators to initiate a decontamination process.

Method of Use

An aspect of the application relates to method of controlling decontamination of a substantially enclosed space, comprising: detecting a micro-organism's presence in a substantially enclosed space, wherein the presence of the micro-organism is sensed by one or more sensors that are present within the substantially enclosed space; alerting a system controller to the presence of the micro-organism in the substantially enclosed space, wherein the system controller is networked to the one or more sensors; informing an operator device of the presence of the micro-organism in the substantially enclosed space, wherein the operator device is networked to the system controller; initiating a decontamination process to remove the presence of the micro-organism in the substantially enclosed space, wherein the decontamination process is applied by one or more applicators networked to the system controller, and further wherein the one or more applicators are present in the substantially enclosed space; and further wherein the system controller initiates the decontamination process by the one or more applicators after the steps of either: (1) ordering the initiation of a decontamination process from the operate device; or (2) ordering the initiation of a decontamination process by an event sub-system, wherein the event sub-system is a non-transitory tangible computer-readable medium comprising instructions to decontaminate a substantially enclosed space.

In certain embodiments, a control system uses a general purpose computer to implement instructions for repeating decontamination cycles of a decontamination apparatus, the instructions comprising: sensing a presence of a pathogen in a substantially enclosed space; communicating the presence of the pathogen to a computer database; identifying the pathogen sensed in the substantially enclosed space using the computer database; selecting a program of decontamination cycles from the computer database based on the identity of the pathogen; communication the selected program to a decontamination apparatus, wherein the decontamination apparatus is networked to automatically follow the program; performing the decontamination cycles according to the program.

Some examples of embodiments using the decontamination apparatus, system, or method of the present disclosure include shipping containers. For example, a shipping container may be equipped with a decontamination system that can sense pathogen load within, or on surfaces of, the container. Exemplary systems can feed information about pathogen load to parties equipped to receive data. In some embodiments, a system can print or record data.

Other examples of embodiments using the decontamination apparatus, system, or method of the present disclosure include import, export, travel quarantine areas or checkpoints. In some embodiments, the system includes a walk-through space or tunnel, conveyer system, moving walkway or any other suitable means for moving persons or objects through the mist generated by the decontamination system.

Still other examples of embodiments using the decontamination apparatus, system, or method of the present disclosure include a vehicle. In some embodiments, the vehicle is a car, truck, bus, train, airplane, or any other form of transportation purposed for the movement of goods or passengers. In further embodiments, the vehicle is an autonomous vehicle.

Yet other examples of embodiments using the decontamination apparatus, system, or method of the present disclosure include space travel, space quarantine, or structures that do not reside on the planet earth.

Some examples of embodiments using the decontamination apparatus, system, or method of the present disclosure include food processing/preparation systems. In some embodiments, the system includes sensors, such as photo-detectors, to activate the apparatus. In some embodiments, the system includes sensors for detecting pathogen load.

Still other examples of embodiments using the decontamination apparatus, system, or method of the present disclosure include self-guiding robots networked wirelessly with the customized engineering system. For example, a self-guiding robot equipped with the decontamination system can move around a space or facility, detect contamination via a single or multiple sensors of the same or different types in response to directions received from the customized engineering system. A self-guiding robot equipped with the decontamination system and networked with the customized engineering system can treat a contaminated surface or space until bioload is reduced in a target area.

Yet other examples of embodiments using the decontamination apparatus, system, or method of the present disclosure include emergency biocontamination rapid deployment chambers.

Other examples of embodiments using the decontamination apparatus, system, or method of the present disclosure include farms, ranches, livestock facilities or abattoirs. As non-limiting examples, a decontamination apparatus or system can be installed in a poultry facility, such as chicken coops, or a dairy collection facility.

Still other examples of embodiments using the decontamination apparatus, system, or method of the present disclosure include, but are not limited to, gyms, studios, training facilities, or bathrooms.

Other examples of embodiments using the decontamination apparatus, system, or method of the present disclosure include buildings with a decontamination system integrated into the building systems in order to decontaminate the entire building or specific area of the building. In some embodiments, the system is integrated into new construction. In other embodiments, the system is integrated into the automation or ventilation systems of an existing building. In some embodiments, a decontamination system or apparatus of the present disclosure is programmable or automated.

Effective disinfection by activated hydroxyl ions as used in the present application depends on the surface area of the droplets that are applied to surfaces; that is the smaller the droplets, the greater the surface area of activated hydroxyl ions on the total cloud of droplets, and thus, the more effective the disinfection method. In fact, soaking a surface for disinfection undermines effectiveness of activated hydroxyl ions because once a surface is soaked the activated ions will not be brought into contact with the bacteria for disinfection.

Activation of the cleaning fluid to produce activated hydroxyl ions may occur through passage of the fluid, for example, an electric are current, an electromagnetic field, or photonic energy. The fluid may be generated as a spray via, for example, nebulization, ultrasonices, pneumatic spray, or mechanical pressure. However, blowers are not used in the method of the application to generate a spray, as a blower will generate a powerful stream of large droplets that will soak a surface with fluid, which both undermines the impact of any activated hydroxyl ions.

The methods of the application require that a very dry mist (very low diameter aerosol particles as described herein) be generated which carries activated hydroxyl ions through a space to a surface for decontamination. The activated hydroxyl ions make contact with pathogens before recombining to form harmless diatomic oxygen and water (it is an advantage of the approach herein that no chemical residue remains on the disinfected surface). Preferred embodiments of the present application use, for example, a cleaning fluid that comprises 0.3% to 9% hydrogen peroxide as a source of an active species for decontamination of an article or substantially enclosed space. Preferred aerosol droplets that carry activated hydroxyl ions are 0.3-1.0 microns in diameter, with most preferred to average 0.7 microns in diameter. Accordingly, any automated systems applying the present methods require exacting parameters for performance.

Methods and technologies preferable for use in decontamination processes are discussed in U.S. Pat. No. 10,391, 188, which is incorporated herein by reference. A decontamination fluid mist is activated to produce an activated decontamination fluid mist. The activation produces activated species of the decontamination fluid material in the mist, such as the decontamination fluid material in the ionized, plasma, or free radical states. At least a portion of the activatable species is activated, and in some cases some of the promoting species, if any, is activated. A high yield of activated species is desired to improve the efficiency of the decontamination process, but it is not necessary that all or even a majority of the activatable species achieve the activated state. Any operable activator may be used. The activator field or beam may be electrical or photonic. Examples include an AC electric field, an AC arc, a DC electric field, a DC arc, an electron beam, an ion beam, a microwave beam, a radio frequency beam, and an ultraviolet light beam produced by a laser or other source. The activator causes at least some of the activatable species of the decontamination fluid in the decontamination fluid mist to be excited to the ion, plasma, or free radical state, thereby achieving "activation". These activated species enter redox reactions with the cell walls of the microbiological organisms, thereby destroying the cells or at least preventing their multiplication and growth. In the case of the preferred hydrogen peroxide, at least some of the H2O2 molecules dissociate to produce hydroxyl (OH—) and monatomic oxygen (O—) ionic activated species. These activated species remain dissociated for a period of time, typically several seconds or longer, during which they attack and destroy the biological microorganisms. The activator is preferably tunable as to the frequency, waveform, amplitude, or other properties of the activation field or beam, so that it may be optimized for achieving a maximum recombination time for action against the biological microorganisms. In the case of hydrogen peroxide, the dissociated activated species recombine to form diatomic oxygen and water, harmless molecules.

Exemplary decontamination devices/systems of the present disclosure comprise an applicator having a cold plasma arc that splits a hydrogen peroxide-based solution into reactive oxygen species, including hydroxyl radicals, that seek, kill, and render pathogens inactive. The activated particles generated by the applicator kill or inactivate a broad spectrum of pathogens and are safe for sensitive equipment. In general, decontamination devices/systems of the present disclosure allow the effective treatment of an exemplary space measuring 104 $m^2$ in about 75 minutes, including application time, contact time, and aeration time. Decontamination devices/systems of the present disclosure are scalable and configurable to be effective in any size or volume of space/room/chamber/container. The scalability may be accomplished by the size of the device, by the manual control of the decontamination fluid, or by programming the air pressure of the device and the consequent fluid flow rate as a function of the input space/room/chamber/container parameters.

Conventional methods of decontamination are less effective in decontaminating closed spaces. This application discloses that decontamination using a very dry mist comprising ionized hydrogen peroxide provides unexpectedly high levels of kill rate of pathogens (which encompasses bacteria, fungi, protozoan or viruses), such as, e.g., *Candida auris*, in small enclosures, semi-enclosed spaces and closed areas (a small enclosure is an area of 12"×12"×12" or less; a semi-enclosed space is an area in which part of a small enclosure is open to other areas; a closed area is an area in which no parts of the small enclosure are open to other areas).

A very dry mist is a mist in which particles have particle size diameter within the ranges of about 0.1-0.2 microns, 0.1-0.3 microns, 0.1-0.4 microns, 0.1-0.5 microns, 0.1-0.6 microns, 0.1-0.7 microns, 0.1-0.8 microns, 0.1-0.9 microns, 0.1-1 microns, 1-1.1 microns, 1-1.2 microns, 1-1.3 microns, 1-1.4 microns, 1-1.5 microns, 1-1.6 microns, 1-1.7 microns, 1-1.8 microns, 1-1.9 microns, 1-2 microns, 0.5-0.6 microns, 0.5-0.7 microns, 0.5-0.8 microns, 0.5-0.9 microns, 0.5-1 microns, 0.5-1.1 microns, 0.5-1.2 microns, 0.5-1.3 microns, 0.5-1.4 microns, 0.5-1.6 microns, 0.5-1.7 microns, 0.5-1.8 microns, 0.5-1.9 microns, 0.5-2 microns, 0.5-2.1 microns, 0.5-2.2 microns, 0.5-2.3 microns, 0.5-2.4 microns, 0.5-2.5 microns, 0.5-2.6 microns, 0.5-2.7 microns, 0.5-2.8 microns, 0.5-2.9 microns, 0.5-3 microns, 0.5-3.1 microns, 0.5-3.2 microns, 0.5-3.3 microns, 0.5-3.4 microns, or 0.5-3.5 microns. In certain embodiments, the very dry mist has particles with particle diameter size in the range of about 0.5-3 microns, preferably on average 0.7 microns.

In certain embodiments, the customized engineering system described herein monitors the size of the aerosol droplets being produced, so that the aerosol droplets carrying activated hydroxyl ions form a very dry mist as described herein. In preferred embodiments, the population of aerosol droplets at least 80%, 90%, 95%, 100% are within the size range of 0.3-1.0 microns in diameter. In particular embodiments, the size of aerosol droplets is monitored by use of laser scanning of aerosol droplet size. Optical measurements may be performed with a sensor or a particle detector placed in the detection zone after the point of activation of hydroxyl ions on the aerosol droplets, sensors may be an optical particle counter (OPC), a laser particle counter (LPC), or a condensation particle counter (CPC). OPCs or LPCs can detect particle sizes larger than 0.1 microns. The customized engineering system is equipped with a computer processor as described herein, which receives data regarding the size range of aerosol droplets carrying activated hydroxyl ions. The customized engineering system is programmed to adjust control parameters governing the size of particles in the very dry mist to maintain the population of aerosol droplet sizes within the desired range.

The customized engineering system includes a programming clock, and provides air pressure control and fluid flow control through use of one or more potentiometers. The programming clock provides the ability to automate cycles of decontamination within a small enclosure. The cycles of decontamination controlled by the programming clock may, for example, include cycles of spraying a very dry mist for thirty seconds, stopping spray for ten seconds, and then re-starting spraying for another thirty seconds, etc. repeating such cycles for a fixed period of time. The programming clock can be set manually by a user or controlled remotely by wireless by the user or a computer processor with pre-programmed decontamination cycles that are transmitted to the device for deployment.

In certain embodiments, the time period during sprayings may be 10-1800 seconds, 10-1200 seconds, 10-900 seconds, 10-600 seconds, 10-300 seconds, 10-180 seconds, 10-150 seconds, 10-120 seconds, 10-90 seconds, 10-60 seconds, 10-45 seconds, 10-30 seconds, 30-1800 seconds, 30-1200 seconds, 30-900 seconds, 30-600 seconds, 30-300 seconds, 30-180 seconds, 30-150 seconds, 30-120 seconds, 30-90 seconds, 30-60 seconds, 30-45 seconds, 60-1800 seconds, 60-1200 seconds, 60-900 seconds, 60-600 seconds, 60-300 seconds, 60-180 seconds, 60-150 seconds, 60-120 seconds, 60-90 seconds, 90-1800 seconds, 90-1200 seconds, 90-900 seconds, 90-600 seconds, 90-300 seconds, 90-180 seconds, 90-150 seconds, 90-120 seconds, 120-1800 seconds, 120-1200 seconds, 120-900 seconds, 120-600 seconds, 120-300 seconds, 120-180 seconds, 120-150 seconds, 150-1800 seconds, 150-1200 seconds, 150-900 seconds, 150-600 seconds, 150-300 seconds, 150-180 seconds, 180-1800 seconds, 180-1200 seconds, 180-900 seconds, 180-600 seconds, 180-300 seconds, 300-1800 seconds, 300-1200 seconds, 300-900 seconds, 300-600 seconds, 600-1800 seconds, 600-1200 seconds, 600-900 seconds, 900-1800 seconds, 900-1200 seconds or 1200-1800 seconds.

In certain embodiments, the time period between two consequent sprayings may be 1-600 seconds, 1-300 seconds, 1-180 seconds, 1-150 seconds, 1-120 seconds, 1-90 seconds, 1-60 seconds, 1-45 seconds, 1-30 seconds, 1-15 seconds, 10-600 seconds, 10-300 seconds, 10-180 seconds, 10-150 seconds, 10-120 seconds, 10-90 seconds, 10-60 seconds, 10-45 seconds, 10-30 seconds, 30-600 seconds, 30-300 seconds, 30-180 seconds, 30-150 seconds, 30-120 seconds, 30-90 seconds, 30-60 seconds, 30-45 seconds, 60-600 seconds, 60-300 seconds, 60-180 seconds, 60-150 seconds, 60-120 seconds, 60-90 seconds, 90-600 seconds, 90-300 seconds, 90-180 seconds, 90-150 seconds, 90-120 seconds, 120-600 seconds, 120-300 seconds, 120-180 seconds, 120-150 seconds, 150-600 seconds, 150-300 seconds, 150-180 seconds, 180-600 seconds, 180-300 seconds, or 300-600 seconds. In one example, the time period between two consequent sprayings is 60 seconds.

In some cases, the time period during spraying is 90 seconds, with 60 second intervals between spraying. In some embodiments, a spray circle comprises a spray time and a break time, and a complete decontamination process comprises 1, 2, 3, 4, 5, 6, 7, 8, 9 or 10 spray circles. (Spray circle=spray+interval−total number of circles.)

In certain embodiments, the customized engineering system will possess a computer processor that can calculate the appropriate settings (e.g., flow rate, air pressure, number and length of decontamination cycles) to produce a very dry mist comprising ionized hydrogen peroxide that will effectively decontaminate a closed space. In such embodiments, the user may enter the parameters of the small enclosure manually to the device, or enter them remotely by a wireless connection. The operation of the system can be fully automated, fully remotely controlled, or may be semi-automated (e.g., uses cycles of decontamination performed automatically according to parameters that have been manually entered).

It is a common problem of the conventional technology that excessive air pressure reduction produces mist particles that are too large to achieve a desired mist/fog profile. At the same time, particularly enclosed spaces often require significant air pressure reduction. These opposing constraints of a decontamination system are addressed by certain embodiments of the present disclosure. Namely, by programming the processor to control the potentiometer based on the input parameters of the small enclosure, a user can regulate a fluid flow rate in synchronization with the air pressure. As a result, reducing the fluid flow rate while simultaneously lowering the air pressure maintains the mist/fog particle size small, while limiting the distance the spray can reach. In this manner, the mist sprayed by the customized engineering system remains within the boundaries of the enclosed space, without creating excessively wet and dense fog. The programmable balance between the air pressure and the fluid flow rate, therefore, prevents saturating surfaces opposite to mist applicators, increased moisture accumulation due to condensation, false negative validation results or increased aeration times of the enclosure.

A Backpack for Decontaminating an Article

An aspect of the application is a backpack for decontaminating an article or substantially enclosed space, comprising the features of: a point-and-spray applicator; shearing a cleaning fluid into a mist comprising aerosol droplets accumulating in a top chamber portion of a substantially closed chamber comprising a funnel shaped top chamber portion, a bottom chamber portion, a side chamber portion and an interior chamber portion, wherein the cleaning fluid is sheared by ultrasonic cavitation; subjecting the mist to a nonthermal plasma actuator to form plasma activated ionic particles, wherein the actuator has posts generating a cold plasma arc; and contacting the article or substantially enclosed space to the plasma activated ionic particles, enhancing decontamination by ionized hydrogen peroxide by lowering the position of the electrodes of the posts generating a cold plasma arc and using a DC voltage source.

An aspect of the application is a backpack for decontaminating an article, surface or substantially enclosed space, comprising the features of: a point-and-spray applicator; shearing a cleaning fluid into a mist comprising aerosol droplets by cavitating the cleaning fluid using an ultrasonic cavitator submerged in a substantially closed chamber comprising the cleaning fluid; subjecting the mist to a nonthermal plasma actuator in an outlet tube extending from an opening in a top chamber portion of the substantially closed chamber, wherein the outlet tube comprises a hollow lumen with a distal opening above the top chamber portion for expelling the aerosol droplets to form plasma activated ionic particles; and contacting the article, surface, or substantially enclosed space with the plasma activated ionic particles, enhancing decontamination by ionized hydrogen peroxide by lowering the position of the electrodes of the posts generating a cold plasma arc and using a DC voltage source.

An aspect of the application is a backpack for decontaminating a small enclosure, comprising the features of: a point-and-spray applicator; entering input parameters of the small enclosure into a processing unit, wherein the processing unit is programmed to determine fluid properties of a cleaning fluid in a backpack based on the input parameters of the small enclosure space, activating a decontamination cycle of the backpack, wherein the decontamination cycle comprises the features of: providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the substantially small enclosure, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by lowering the position of the electrodes of the posts generating a cold plasma arc and using a DC voltage source.

An aspect of the application is a system for decontaminating a small enclosure, comprising a backpack; a point-and-spray applicator; and a computer processor, wherein the computer processor is in networked communication with the backpack, wherein input parameters of the small enclosure space are entered into the computer processor, wherein the computer processor is programmed to determine fluid properties of a cleaning fluid in the backpack based on the input parameters of the small enclosure space, wherein the computer processor is further programmed to activate a decontamination cycle of the backpack, the decontamination cycle comprising the features of: providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the substantially small enclosure space, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by lowering the position of the electrodes of the posts generating a cold plasma arc and using a DC voltage source.

In certain embodiments, a user is operating the backpack manually. In certain embodiments, the backpack is hand-held to be operated manually. In certain embodiments, the input parameters of the small enclosure comprise: dimensions of the small enclosure space, a position of the backpack relative to boundaries of the small enclosure space, air temperature, pressure, and humidity of the small enclosure. In certain embodiments, the set fluid properties of the cleaning fluid comprise air pressure and fluid flow rate. In certain embodiments, the air valve is controlled by programming the processing unit to control a potentiometer. In certain embodiments, the determined fluid properties of the cleaning fluid are adjusted by a size and a shape of a tube located at an exit of the cleaning fluid out of the backpack. In certain embodiments, the very dry mist comprises particles of diameter size in the range of 0.1-0.7 microns. In certain embodiments, the fluid properties of the cleaning fluid are set by lowering the air pressure and the fluid flow rate respectively below a predetermined standard air pressure and a predetermined standard fluid flow rate. In certain embodiments, the user is entering input parameters of a small enclosure into a processing unit, wherein the processing unit is further programmed to determine the fluid properties of the cleaning fluid in the backpack based on the input parameters of the small enclosure. In certain embodiments, the very dry mist comprises particles of diameter size in the range of 0.1-0.7 microns. In certain embodiments, the input parameters of the small enclosure are manually input. In certain embodiments, the input parameters of the small enclosure are measured by a plurality of sensors that are in networked communication with the processing unit. In certain embodiments, the processing unit and the backpack are in wireless communication.

A Low Flow Nozzle Body for Decontaminating an Article

An aspect of the application is a low flow nozzle body for decontaminating an article or substantially enclosed space, comprising the features of: a general purpose applicator; shearing a cleaning fluid into a mist comprising aerosol droplets accumulating in a top chamber portion of a substantially closed chamber comprising a funnel shaped top chamber portion, a bottom chamber portion, a side chamber portion and an interior chamber portion, wherein the cleaning fluid is sheared by ultrasonic cavitation; subjecting the mist to a nonthermal plasma actuator to form plasma activated ionic particles, wherein the actuator has posts generating a cold plasma arc; and contacting the article or substantially enclosed space to the plasma activated ionic particles, enhancing decontamination by ionized hydrogen peroxide by lowering the position of the electrodes of the posts generating a cold plasma arc and using a DC voltage source.

An aspect of the application is a low flow nozzle body for decontaminating an article, surface or substantially enclosed space, comprising the features of: a general purpose applicator; shearing a cleaning fluid into a mist comprising aerosol droplets by cavitating the cleaning fluid using an ultrasonic cavitator submerged in a substantially closed chamber comprising the cleaning fluid; subjecting the mist to a nonthermal plasma actuator in an outlet tube extending from an opening in a top chamber portion of the substantially closed chamber, wherein the outlet tube comprises a hollow lumen with a distal opening above the top chamber portion for expelling the aerosol droplets to form plasma activated ionic particles; and contacting the article, surface, or substantially enclosed space with the plasma activated ionic particles, enhancing decontamination by ionized hydrogen peroxide by lowering the position of the electrodes of the posts generating a cold plasma arc and using a DC voltage source.

An aspect of the application is a low flow nozzle body for decontaminating a small enclosure, comprising the features of: a 90 degree applicator; entering input parameters of the small enclosure into a processing unit, wherein the processing unit is programmed to determine fluid properties of a cleaning fluid in a low flow nozzle body based on the input parameters of the small enclosure space, activating a decontamination cycle of the low flow nozzle body, wherein the decontamination cycle comprises the features of: providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the substantially small enclosure, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by lowering the position of the electrodes of the posts generating a cold plasma arc and using a DC voltage source.

An aspect of the application is a system for decontaminating a small enclosure, comprising a low flow nozzle body; a general purpose applicator; and a computer processor, wherein the computer processor is in networked communication with the low flow nozzle body, wherein input parameters of the small enclosure space are entered into the computer processor, wherein the computer processor is programmed to determine fluid properties of a cleaning fluid in the low flow nozzle body based on the input parameters of the small enclosure space, wherein the computer processor is further programmed to activate a decontamination cycle of the low flow nozzle body, the decontamination cycle comprising the features of: providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the substantially small enclosure space, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by lowering the position of the electrodes of the posts generating a cold plasma arc and using a DC voltage source.

An aspect of the application is a low flow nozzle body for decontaminating spaces, the low flow nozzle body comprising the features of: a general purpose applicator; entering input parameters of a space into a processing unit, wherein the processing unit is programmed to determine fluid properties of a decontamination fluid in an ionization/aerosolization and activation device based on the input parameters of the space containing said fresh produce, wherein the decontamination fluid comprises hydrogen peroxide, activating a decontamination cycle of the ionization/aerosolization and activation device, wherein the decontamination cycle comprises the features of: providing a reservoir of the decontamination fluid; setting the determined fluid properties of the decontamination fluid; generating a very dry mist comprising ionized/aerosolized hydrogen peroxide of the decontamination fluid, wherein an ionized/aerosolized mist of hydrogen peroxide of the decontamination fluid is passed through a cold plasma arc, wherein the mist is ionized by the cold plasma arc so that the mist comprises ionized/aerosolized particles in the nanosized range of mean diameter 40.3 nm, a mode of 33.4 nm and a standard deviation of 30.9 nm, and the very dry mist is a mist in which particles have particle size diameter within the ranges of 0.1-0.9 microns; applying the generated very dry mist to surfaces within the space, wherein the ionized/aerosolized hydrogen peroxide dissociates to form diatomic oxygen and water on the surfaces, and wherein after thirty minutes from passing through the cold plasma arc into the space containing fresh produce the ionized/aerosolized particles in the nanosized range continue to persist in the space containing fresh produce, enhancing decontamination by ionized hydrogen peroxide by lowering the position of the electrodes of the posts generating a cold plasma arc and using a DC voltage source.

In certain embodiments, the user is operating the low flow nozzle body manually. In certain embodiments, the low flow nozzle body is hand-held to be operated manually.

In certain embodiments, the input parameters of the small enclosure comprise: dimensions of the small enclosure space, a position of the low flow nozzle body relative to boundaries of the small enclosure space, air temperature, pressure, and humidity of the small enclosure.

In certain embodiments, the user is operating the low flow nozzle body manually. In certain embodiments, the low flow nozzle body is hand-held to be operated manually. In certain embodiments, the input parameters of the small enclosure comprise: dimensions of the small enclosure space, a position of the low flow nozzle body relative to boundaries of the small enclosure space, air temperature, pressure, and humidity of the small enclosure. In certain embodiments, the set fluid properties of the cleaning fluid comprise air pressure and fluid flow rate. In certain embodiments, the air valve is controlled by programming the processing unit to control a potentiometer. In certain embodiments, the determined fluid properties of the cleaning fluid are adjusted by a size and a shape of a tube located at an exit of the cleaning fluid out of the low flow nozzle body. In certain embodiments, the very dry mist comprises particles of diameter size in the range of 0.1-0.7 microns. In certain embodiments, the fluid properties of the cleaning fluid are set by lowering the air pressure and the fluid flow rate respectively below a predetermined standard air pressure and a predetermined standard fluid flow rate. In certain embodiments, the use includes entering input parameters of a small enclosure into a processing unit, wherein the processing unit is further programmed to determine the fluid properties of the cleaning fluid in the low flow nozzle body based on the input parameters of the small enclosure. In certain embodiments, the very dry mist comprises particles of diameter size in the range of 0.1-0.7 microns. In certain embodiments, the input parameters of the small enclosure are manually input. In certain embodiments, the input parameters of the small enclosure are measured by a plurality of sensors that are in networked communication with the processing unit. In certain embodiments, the set fluid properties of the cleaning fluid comprise air pressure and fluid flow rate. In certain embodiments, the air valve is controlled by programming the processing unit to control a potentiometer. In certain embodiments, the determined fluid properties of the cleaning fluid are adjusted by a size and a shape of a tube located at an exit of the cleaning fluid out of the low flow nozzle body. In certain embodiments, the very dry mist comprises particles of diameter size in the range of 0.1-0.7 microns. In certain embodiments, the fluid properties of the cleaning fluid are set by lowering the air pressure and the fluid flow rate respectively below a predetermined standard air pressure and a predetermined standard fluid flow rate. In certain embodiments, use includes entering input parameters of a small enclosure into a processing unit, wherein the processing unit is further programmed to determine the fluid properties of the cleaning fluid in the low flow nozzle body based on the input parameters of the small enclosure. In certain embodiments, the very dry mist comprises particles of diameter size in the range of 0.1-0.7 microns. In certain embodiments, the input parameters of the small enclosure are manually input. In certain embodiments, the input parameters of the small enclosure are measured by a plurality of sensors that are in networked communication with the processing unit.

The present application is further illustrated by the following examples that should not be construed as limiting. The contents of all references, patents, and published patent applications cited throughout this application, as well as the Figures and Tables, are incorporated herein by reference.

EXAMPLES

Example 1

In a first test series, identical cultures of *Serratia marcenscens* were prepared by plating onto filter papers. One specimen was incubated for 24 hours at 30° C. in air as a control. Significant growth of the bacteria culture was observed. A second specimen was exposed to a 3 percent by volume aqueous hydrogen peroxide mist (which had not been activated) for 60 seconds in air at one atmosphere pressure, and thereafter incubated for 24 hours at 30° C. in air. Significant growth of the bacteria culture was observed. A third specimen was exposed to a 3 percent by volume aqueous hydrogen peroxide mist, which had been activated by passage through a 10.5 kilovolt AC arc, for 60 seconds in air at one atmosphere pressure, and thereafter incubated for 24 hours at 30° C. in air at one atmosphere pressure. This specimen showed no growth of the bacteria culture, which was killed by the treatment. After this demonstration that the activation treatment rendered the 3 percent hydrogen peroxide mist capable of preventing growth, additional respective specimens were tested using 1.5 percent, 0.75 percent, 0.3 percent, and 0 percent ("activated" water vapor only) concentration hydrogen peroxide mists for 60 seconds exposure in air at one atmosphere pressure, and incubated as described. The specimens contacted by the 1.5 percent and 0.75 percent hydrogen peroxide mists showed no growth. The specimen contacted by the 0.3 percent hydrogen peroxide mist showed very slight growth. The specimen contacted by the 0 percent hydrogen peroxide mist showed significant growth of the bacteria culture.

Example 2

For a second and third test series, a duct-simulation structure was built. The duct-simulation structure was a pipe about 10 inches in diameter and 10 feet long, oriented vertically. The mist generator and activator were positioned at the top of the pipe, and a fan operating at about 350-400 cubic feet per minute gas flow was positioned at the bottom of the pipe to induce a gas flow downwardly through the pipe. Test ports were located at 1 foot, 2 feet, 4 feet, and 6 feet from the top of the pipe, and specimens to be tested were inserted at the various ports.

In the second test series, bacterial spore strips (each about ¾ inch long and ¼ inch wide) impregnated with about 106 spores per strip of *Bacillus stearothermophilus* were placed in each of the test ports of the duct-simulation structure. After testing, the specimens were incubated at 50° C. for seven days. In the first test specimen series, air only (no hydrogen peroxide) was flowed over the specimens for 15 seconds. Significant growth of the bacteria culture at all test ports was observed after incubation. In the second specimen series, a 6 percent by volume hydrogen peroxide mist was generated, but not activated, and flowed over the specimens for 15 seconds. The same significant growth of the bacteria culture at all test ports was observed as for the first test specimen series. In the third specimen series, this procedure was repeated, but the 6 percent hydrogen peroxide mist was activated by a 15 kilovolt AC arc. No growth of the bacteria culture was observed at any of the test ports. These results for *Bacillus stearothermophilus* are significant, because this bacteria is known to be resistant to growth control using conventional, low percentage non-activated hydrogen peroxide treatments.

Example 3

In the third test series, bacterial spore strips like those described above were used, except that the bacteria was *Bacillus subtilis* var. *niger. Bacillus subtilis* var. *niger* is a recognized proxy for *Bacillus anthracis*, which is in the same genus and which causes anthrax. Because of its similarity to *Bacillus anthracis, Bacillus subtilis* var. *niger* is used in laboratory testing to study growth of anthrax and its control, without the risk of contracting or spreading anthrax. In the first test specimen series, air only (no hydrogen peroxide) was flowed over the specimens for 15 seconds. Significant growth of the bacteria culture was observed after incubation of specimens from all ports. In the second specimen series, a 6 percent by volume hydrogen peroxide mist was generated, but not activated, and flowed over the specimens for 15 seconds. The same significant growth of the bacteria culture was observed at all ports as for the first test specimen series. In the third specimen series, this procedure was repeated, but the 6 percent hydrogen peroxide mist was activated by passage through a 15 kilovolt AC arc. No growth of the bacteria culture was observed at any of the ports. This testing established that this approach controls the growth of the anthrax proxy in the duct simulation structure.

Example 4

In further testing, ultrasonic cavitation of the cleaning fluid to generate a low pressure, low air flow mist resulted in superior kill.

A 16×16×16 inch box was built for this testing, with the nozzle of the decontamination apparatus penetrating the bottom of the box in the center of the bottom panel.

6-Log biological (*Geobacillus stearothermophilus*) and chemical (iodine $H_2O_2$) indicators were placed in the center of all of the vertical panels. Biological and chemical indicators were also placed on the bottom panel of the box, immediately next to the nozzle.

Activated mist was injected into the box for one minute and allowed to dwell for five minutes.

The biological indicators were then removed from the box and incubated for 7 days. Following incubation, the biological indicators were examined and exhibited 6 log kill of the bacteria.

Although a particular embodiment has been described in detail for purposes of illustration, various modifications and enhancements may be made without departing from the spirit and scope of the application. Accordingly, the application is not to be limited by the described embodiments.

Example 5

In an efficacy test, the decontamination device/system of the present disclosure was tested against a variety of bacterial spores and gram-negative bacteria (including multiple drug resistant organisms, gram-positive bacteria, mold and viruses. Using procedures described in the present disclosure, the $log^{10}$ reduction of the organisms in the following table were determined:

| Organism | Classification | Log Reduction |
|---|---|---|
| *Bacillus atrophaeus* (surrogate for *B. anthracic*) | Bacterial spore | >8.3 |
| *Geobacillus stearotherophilus* | Bacterial spore | >6.3 |
| *Bacillus subtilis* | Bacterial spore | >6.0 |
| *Clostridium difficile* | Bacterial spore | >6.0 |
| *Escherichia coli* | Gram Negative | >7.4 |
| *Pseudomonas aeruginosa* | Gram Negative | >6.0 |
| *Serratia marcescens* | Gram Negative | >6.0 |
| *Salmonella entercia* | Gram Negative | >5.5 |
| *Staphylococcus aureus* | Gram Positive | >7.4 |
| Methicillin- resistant *Staphylococcus aureus* | Gram Positive | >5.9 |
| *Bacillus atrophaeus* vegetative cells | Gram Positive | >9.0 |
| *Aspergillus niger* | Mold | >8.0 |
| *Aspergillus* species | Mold | >7.0 |
| *Cladosporium* species | Mold | >7.0 |
| *Penicillium* species | Mold | >7.0 |
| *Stachybotrys chartarum* | Mold | >7.0 |
| *Trichophyton mentagrophytes* | Mold | >6.0 |
| Human rhinovirus 16 (surrogate for human influenza) | Virus | >6.8 |
| Influenza A (H1N1) | Virus | >10 |
| Norovirus | Virus | >6.4 |
| Adenovirus | Virus | >5.8 |

The results presented in the table show that the decontamination device/system of the present disclosure is an effective broad-spectrum surface and air disinfectant/decontaminant. It is effective against, bacterial spores, gram-negative bacteria, gram-positive bacteria, multiple drug resistant organisms, mold and viruses. The decontamination device/system is effective for mold mitigation and remediation, as well as the elimination of bacteria and viruses.

The decontamination cycle discussed herein relates to the conversion of hydrogen peroxide solution to ionized hydrogen peroxide after passing through an atmospheric cold plasma arc. Ionized hydrogen peroxide contains a high concentration of reactive oxygen species composed mostly of hydroxyl radicals. Reactive oxygen species damage pathogenic organisms through oxidation of proteins, carbohydrates, and lipids. This leads to cellular disruptions and/or dysfunction and allows for disinfection/decontamination in targeted areas, including large spaces.

In certain embodiments for direct application onto surfaces, the particle size for the ionized hydrogen peroxide is 0.5-3 microns, flow rate is 50 ml per minute, dose application is 1 ml per square foot, with an application time of 5 seconds over per square foot of treatment area, and a contact time of 7 minutes to disinfect/decontaminate high touch surfaces. In particular embodiments, the solution used is formulated as silver, chlorine and peracetic acid free, which maximizes material compatibility on rubber, metals, and other surfaces. In other embodiments, effective whole room treatment can be achieved in under 45 minutes for a room which is over 3500 cubic feet. In such embodiments, flow rate may be 25 ml per minute per applicator used (which depends on room size), dose application is 0.5 ml per cubic foot. The room is safe to enter once hydrogen peroxide is below 0.2 ppm. Treatment time, dosage, dwell time, etc, can be varied to suit the desired decontamination goals of the user.

Example 6

In one example for direct application onto surfaces, a small enclosed space is decontaminated. The dimensions of the small container used for the treatment are 12" by 12" by 12". One of the objectives of the example is to maintain the particle size for the decontamination mist/fog sufficiently small (e.g., 0.5-3 microns) in order to avoid excessively dense fog resulting in increased moisture accumulation and aearation time, thus causing false negative validation results. In this example, four injections are performed with 60 seconds between each two consequent injections, and a pulsing program runs for approximately 90 seconds during each injection. Considering the reduced size of the container, the air pressure within the decontamination device is reduced well below the standard pressure range (e.g., 25-50 psi) to 15 psi. In order to prevent the pressure reduction from producing undesirably large sizes of mist/fog particles, the fluid flow rate is also reduced well below the standard range flow rate (e.g., 25-50 ml per minute) to 10-12 ml per minute. Treatment time, dosage, dwell time, etc, can be varied to suit the desired decontamination goals of the user. This very dry mist unexpectedly results in a enhanced kill rate of pathogens on surfaces of the small enclosure.

Example 7

The Applicant has improved the efficacy of breaking the double bond of its cleaning solution by redesigning the following aspects. Lowering the electrode posts in the applicator and changing the arc's power source from AC voltage to DC voltage. Lowering the electrode posts puts the arc discharge into a more effective position for activating the cleaning solution prior to dispersion into the treatment area. Changing the arc's power source from AC voltage to DC voltage increases the homogenous charge characteristics of the droplets. This causes a greater percentage of the droplets to repel each other and seek equilibrium. It also increases air ionization, making it easier for the charged droplets to contact surfaces.

Figure 28:
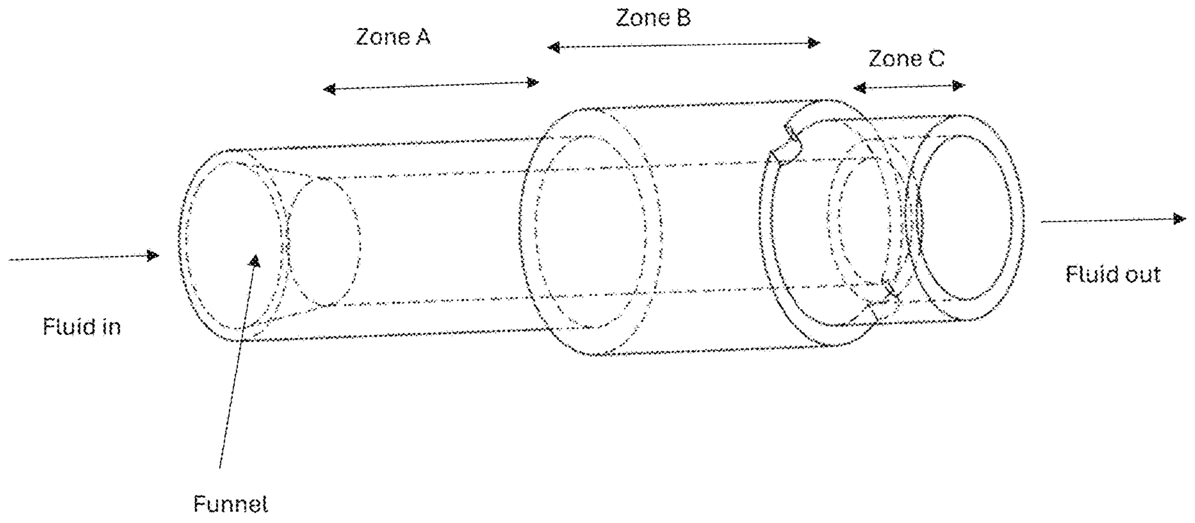
FIG. 28 shows an embodiments of a nozzle as described herein.
Figure 29:
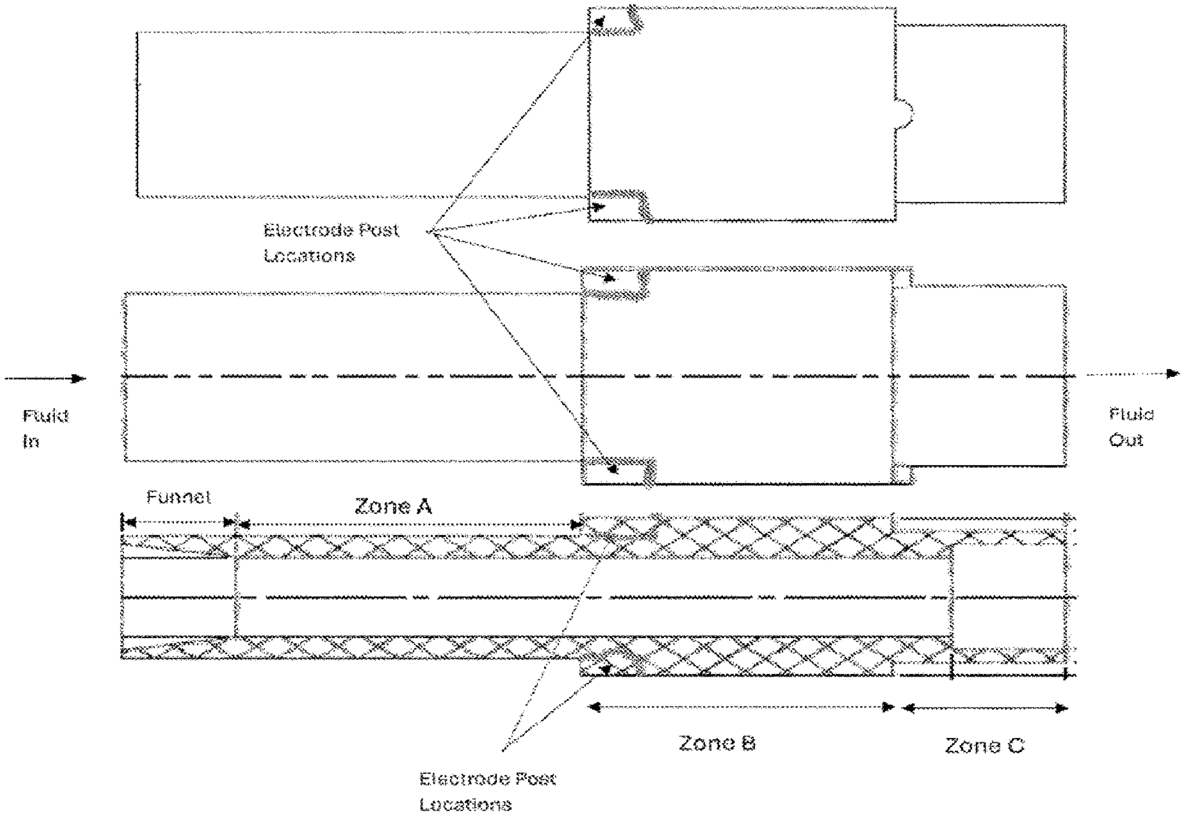
FIG. 29 shows an embodiments of a nozzle as described herein showing the positioning of electrode posts after lowering.

Lowering the electrode post positions the electrodes closer to the cleaning fluid solution as it exits the nozzle in stream before the stream fully combines with the air and becomes a mist in the atmosphere, and creates a fan pattern. In one embodiment, the user flows the mist of the cleaning fluid solution through a funnel in a nozzle body, wherein the nozzle body comprises the funnel; a first zone A, wherein the first zone A, wherein zone A has the same interior diameter as that of the funnel at the funnel's narrowest interior diameter; a second zone B, wherein zone B follows zone A and has solid walls of greater thickness than zone A (creating an exterior step pattern between zone A and zone B, and optionally zone B and zone C), wherein the mists flows through zone B from zone A, and wherein the interior diameter of zone B through which the mist flows is the same interior diameter as the interior diameter of zone A; a third zone C, wherein zone C receives the mist from zone B, wherein the initial interior diameter of zone C is the same as the interior diameter of zone B, and wherein the final interior diameter of zone C is greater than the interior diameter of zone B; and wherein electrode posts are positioned within zone B at a location adjacent to a border between zone A and zone B and wherein there is a gap between the location of the electrode posts and the beginning of zone C (see FIGS. 28 and 29). The lowering of the electrode post, in conjunction with using a DC voltage transformer to create cold plasma arc has shown to convert more of the cleaning fluid solution to hydroxyl radicals and reactive oxygen species through the use of measuring the PPM level of the residual $H_2O_2$ content of the cleaning fluid solution during aeration. Multiple cycles injecting the same volume of cleaning fluid solution into the same space with the same cubic volume, under the same conditions has shown unexpectedly improved results consistently within the 5%+/−capabilities of the system.

Example 8

The backpack format delivers ionized Hydrogen Peroxide (iHP) technology in the most compact form. Featuring a custom backpack form for premium comfort, direct and battery-powered operation, and a smaller cartridge size, the backpack format was designed to facilitate everything from disinfecting facility surfaces to isolated sites. The backpack format features comfortable, highly-adjustable padded straps, compact 32 oz. BIT Solution cartridges, a rechargeable battery, and a streamlined interface that includes simple analog switches for powering on and off and selecting either priming or spraying modes.

As with every decontamination unit, iHP technology ionizes BIT solution by passing through a cold plasma arc, simulating natural disinfection by creating a 360° mist of microscopic particles that kill on contact to deliver quick, six-log surface decontamination.

The backpack format produces six-log and greater reduction in microbial populations, while producing particles with diameters between submicrons to three microns, and is applied at a rate of five seconds per square foot. The backpack runs on 110-230V or 12V battery with a runtime of 75 minutes, and has a single applicator integrated to the backpack. The cartridge volume is thirty-two ounces, with the overall weight of approximately 16.2 lbs and dimensions of 20.5×15×6.5 inches and cord length of four feet.

Example 9

Figure 23:
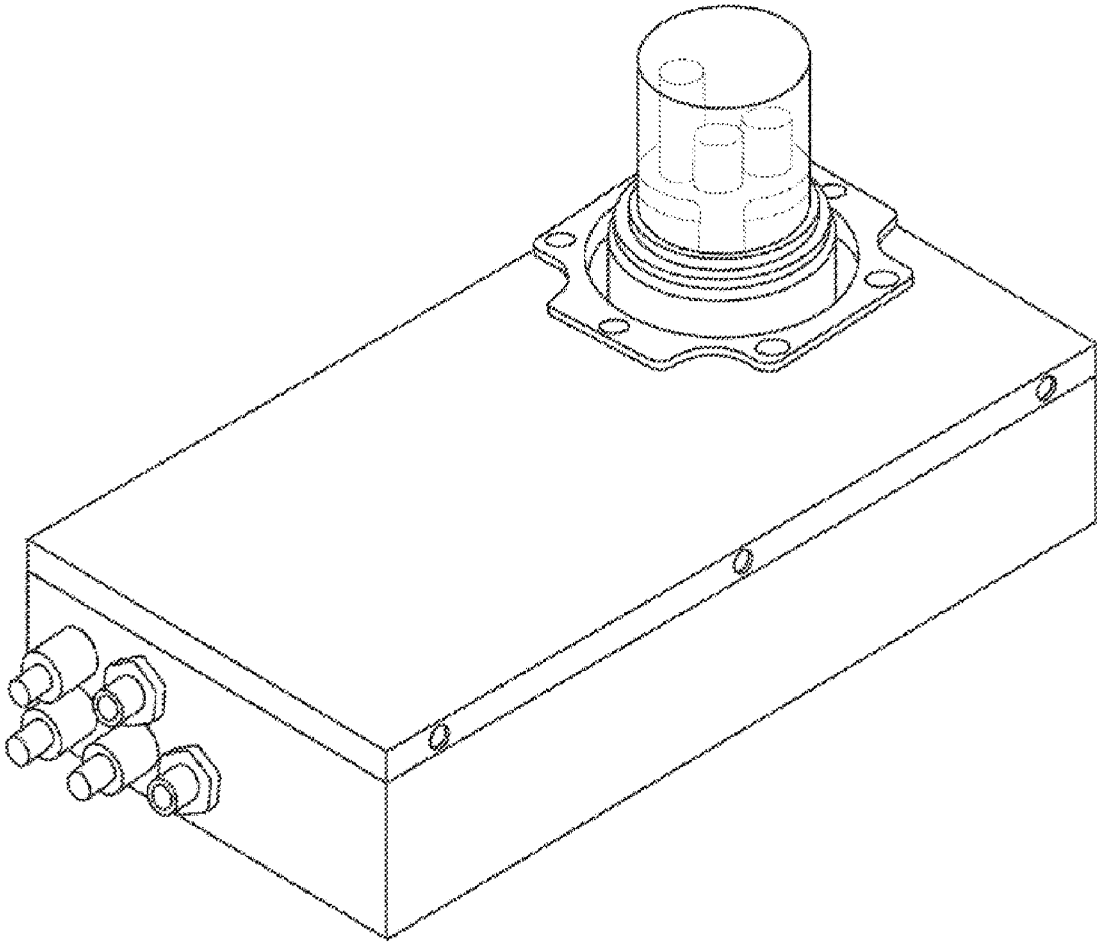
FIG. 23 shows an applicator design for decontamination of a closed space from an external viewpoint.
Figure 24:
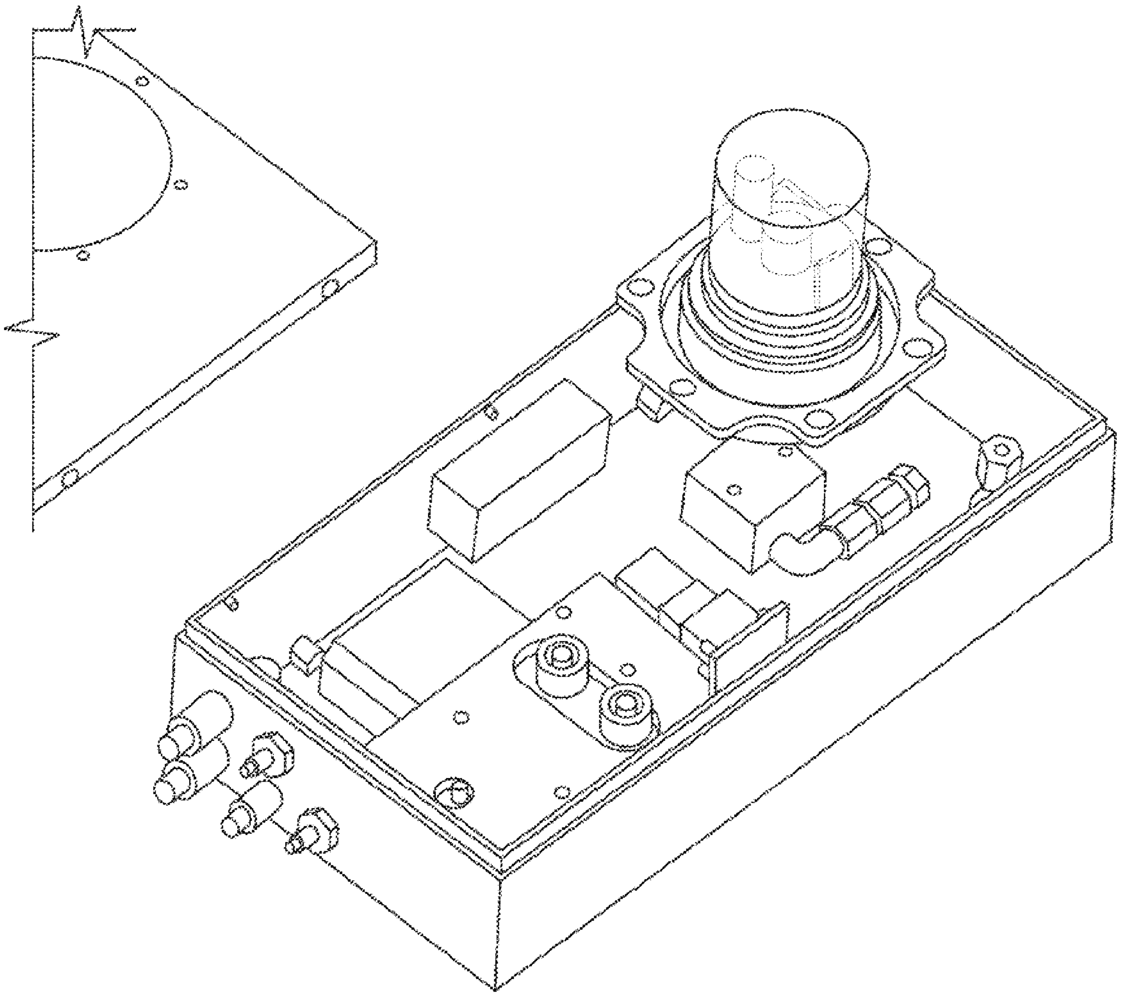
FIG. 24 shows an applicator design for the same applicator showing the internal arrangements.

A custom closed space was created for a 90-degree applicator (see FIG. 23). The enclosure included the Keyence Flow Meter. The Keyence flow meter has greater range. The usual McMillian Flow Meter can only reduce to 13 ml/min. The Keyence can range as low as 2 ml/min.

When injecting into smaller spaces, utilizing low flow rates are required. While using the earlier nozzle bodies, an intermediate pulsation at low flow rates was observed because of a cavity within the nozzle and the nozzle body. To fix the problem it was necessary to eliminate the cavity, so there was a direct flow into the nozzle. Eliminating all cavities apart from that through which the very dry mist flows yielded a consistent flow as low as 2 ml/min.

A Deiner pump was used to achieve these lower flow rates within the system. Doing so also allowed lowering of the air pressure so that the pressure within the closed space was kept neutral. The Diener pump also provided a greater range in reducing as low as 2 ml/mi, vs the KNF pump, which is for higher ranges.

Figure 25A:
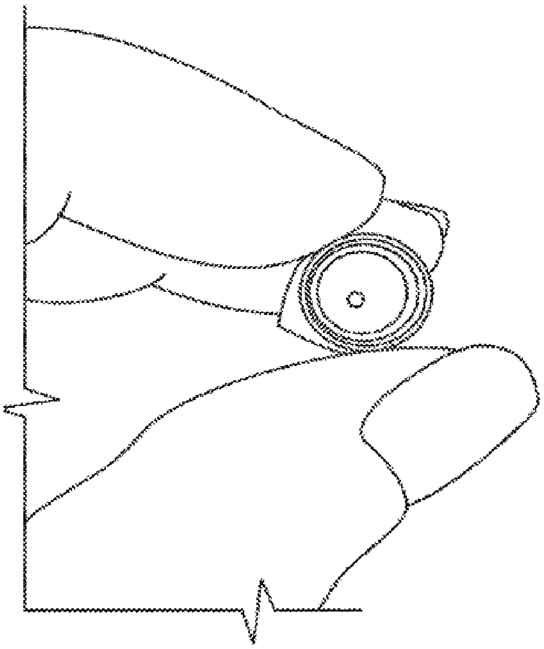
FIG. 25A shows a fitting.
Figure 25B:
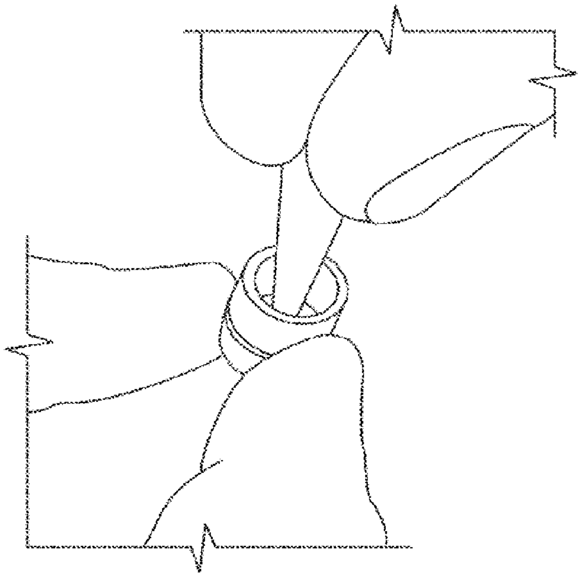
FIG. 25B shows the process of potting the fitting to reduce internal diameter.

The earlier nozzle body was using ¼" tubing/fitting, the self-cleansing nozzle body fitting is for ⅛". The smaller size allowed for a steady stream of fluid at low flow rates. This modification helps with low-flow applications to remove a cavity that improves the spray consistency when reducing the flows at 2-3 ml/min. The previous tubing size was meant for higher flows at an average of 25 ml/min. In addition, another change to the nozzle body that was done was potting the fitting to reduce the internal diameter size of the fitting (see FIG. 25A). The modification was potting this this fitting with the tube with epoxy (see FIG. 25B).

Figure 26A:
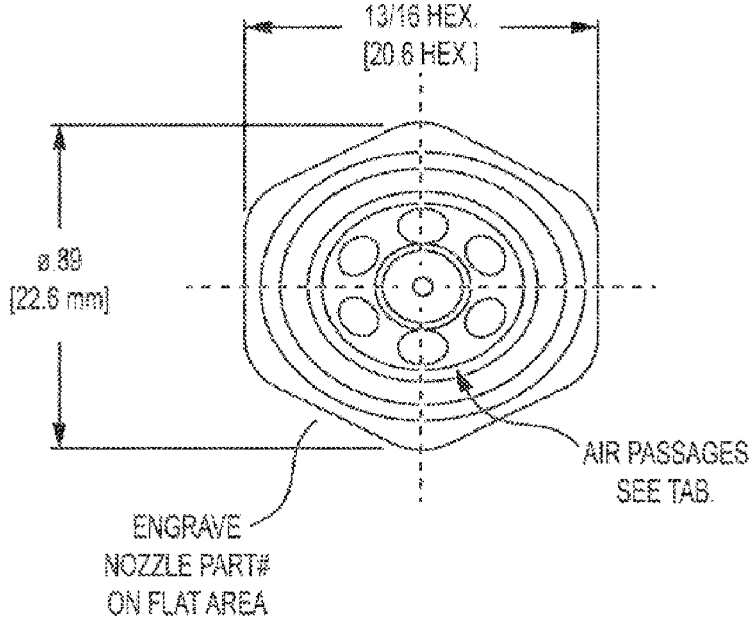
FIG. 26A shows front view of self-cleaning nozzle.
Figure 26B:
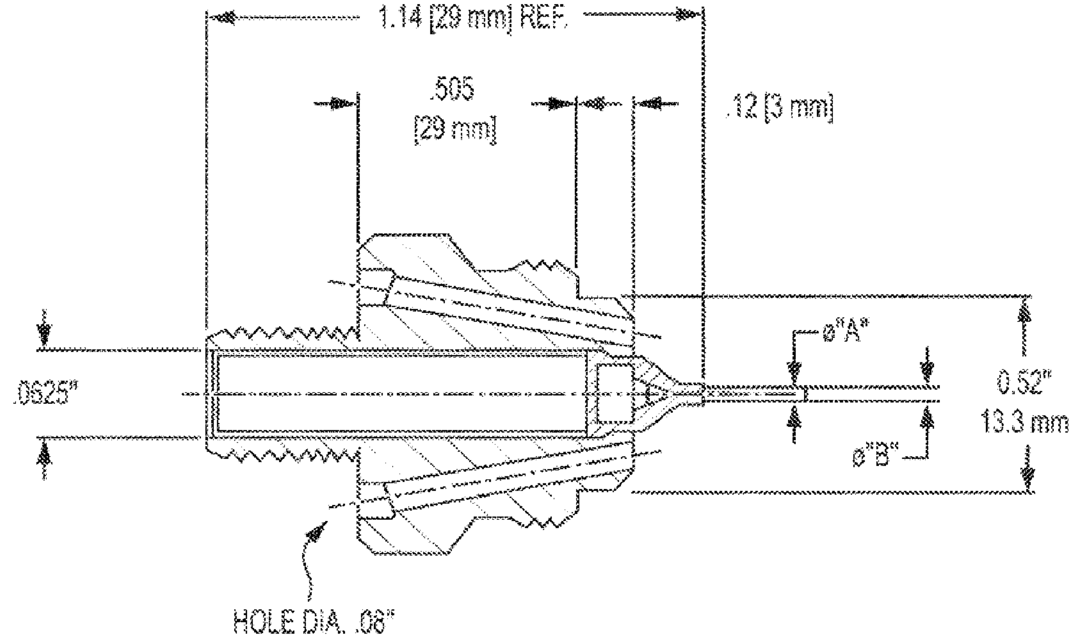
FIG. 26B shows side view of self-cleaning nozzle.
Figure 27:
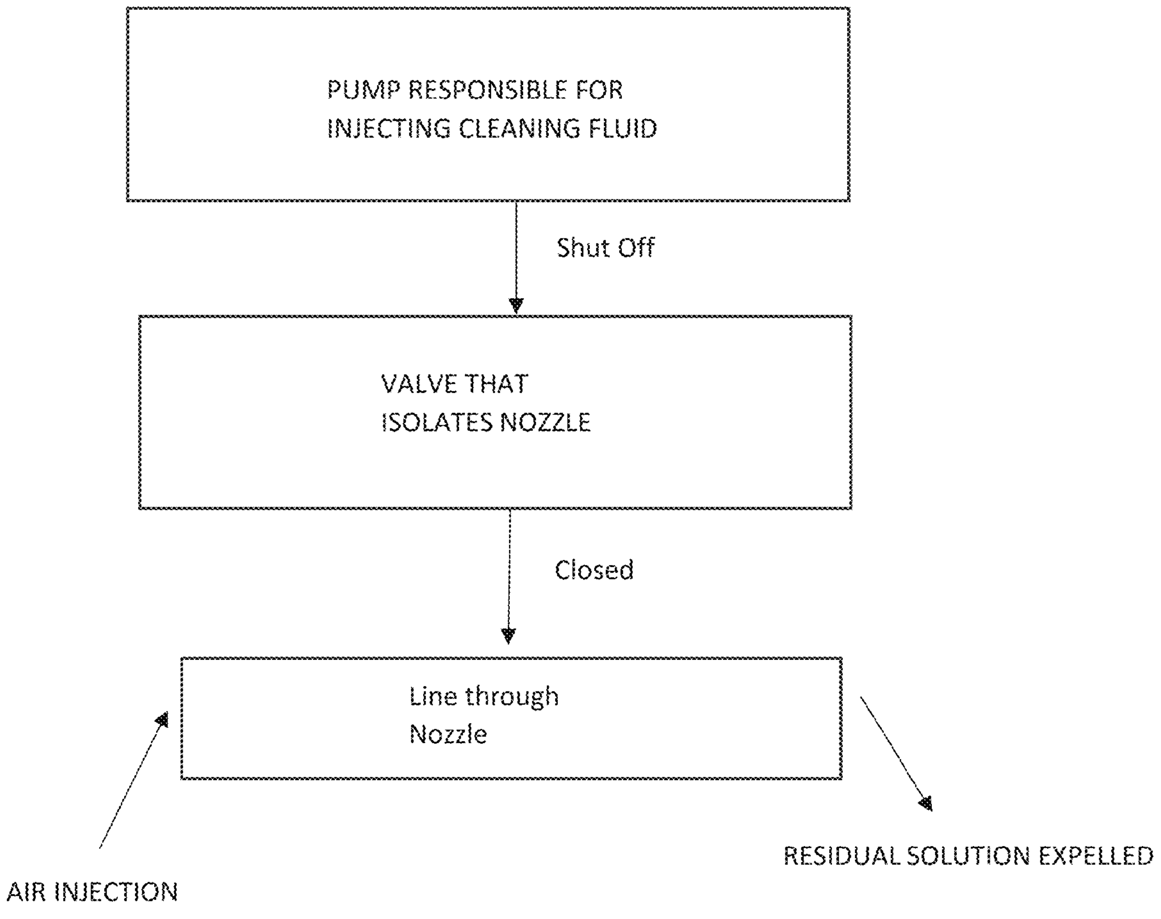
FIG. 27 shows the operation of a self-cleaning nozzle.

To further increase the efficacy, a smaller droplet size was implemented by using a 1050 or 850 nozzle instead of 1450. Previously the 1050 (μm) or 850 nozzle could not be used with this application because of clogging issues. A self-cleaning nozzle was implemented to address this. The self-cleaning nozzle thread hole was changed to 0.0625" (see FIGS. 26A and 26B). At the end of an injection cycle, the pump was shut off, the valve that isolates the nozzle was closed, and then air was injected into that line to blow out any residual solution (see FIG. 27). This makes the nozzle self-cleaning and eliminated any clogs within a nozzle as small as 1050 or even an 850 nozzle could obtain. The inner diameter of both the barbed fluid fitting for the base nozzle body and the 1450 nozzle has been adjusted from ¼ in to 1/16 in to address past pulsing issues experienced during low flow settings. With these modifications, a stable spray can be maintained even at flow rates as low as 3 ml per minute or below.

Example 10

Small-pulsed injections techniques were applied for the application that allows the mist to move around freely and contact surfaces more reliably with temperatures that are not at nominal temperatures. For cold area application a 1050 nozzle was used (depending on air pressure droplet may range in size from 30 to 60 micrometers diameter) with a flow rate of 9 ml/min or lower, with air pressure in range of between 25-35 psi. Bursts of spray were in three cycles, with each burst between 30-45 seconds long and a one minute interval between them to enable dispersion of the mist onto surfaces. The temperature range in the cold area was between 5° C. to −20° C.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A system for decontaminating a small enclosed space, comprising a decontamination device and a computer processor, wherein the computer processor is in networked communication with the decontamination device, wherein input parameters of the small enclosed space are entered into the computer processor, wherein the computer processor is programmed to determine fluid properties of a cleaning fluid in the decontamination device based on the input parameters of the small enclosed space, wherein the computer processor is further programmed to activate a decontamination cycle of the decontamination device, the decontamination cycle comprising the steps of:

providing a reservoir of the cleaning fluid; setting the determined fluid properties of the cleaning fluid; generating a very dry mist comprising ionized hydrogen peroxide of the cleaning fluid, dispersing the very dry mist by high voltage actuation, wherein the very dry mist comprises particles having a particle size diameter within the ranges of 0.1-0.9 microns, wherein the generated very dry mist is applied to decontaminate the small enclosed space, wherein the ionized hydrogen peroxide dissociates to form diatomic oxygen and water, wherein the setting of the determined fluid properties to the cleaning fluid is performed by controlling an air valve, enhancing decontamination by ionized hydrogen peroxide by internalizing within a nozzle body the position of a set of electrode posts generating a cold plasma arc and using a DC voltage source, wherein further comprising flowing the mist through a funnel in the nozzle body, wherein the nozzle body comprises the funnel; a first zone A, wherein zone A has solid walls and a same interior diameter as that of the funnel at the funnel's narrowest interior diameter; a second zone B, wherein zone B follows zone A and has solid walls of greater thickness than zone A, wherein the mist flows through zone B from zone A, and wherein an interior diameter of zone B through which the mist flows is the same interior diameter as the interior diameter of zone A; a third zone C, wherein zone C receives the mist from zone B, wherein an initial interior diameter of zone C is the same as the interior diameter of zone B, and wherein a final interior diameter of zone C is greater than the interior diameter of zone B; and wherein electrode posts are positioned within zone B at a location adjacent to a border between zone A and zone B, wherein the mist flows through the cold plasma arc generated by the electrode posts before flowing into zone C and wherein there is a gap between the location of the electrode posts and the beginning of zone C.

2. The system of claim 1, wherein the decontamination device is operated manually.

3. The system of claim 2, wherein the decontamination device is hand-held to be operated manually.

4. The system of claim 1, wherein the decontamination device is hand-held to be operated manually.

5. The system of claim 1, wherein the input parameters of the small enclosed space comprise: dimensions of the small enclosed space, a position of the decontamination device relative to boundaries of the small enclosed space, air temperature, pressure, and humidity of the small enclosed space.

6. The system of claim 1, wherein the set fluid properties of the cleaning fluid comprise air pressure and fluid flow rate.

7. The system of claim 1, wherein the air valve is controlled by programming the processing unit to control a potentiometer.

8. The system of claim 1, wherein the determined fluid properties of the cleaning fluid are adjusted by a size and a shape of a tube located at an exit of the cleaning fluid out of the decontamination device.

9. The system of claim 1, wherein the very dry mist comprises particles of diameter size in the range of 0.1-0.7 microns.

10. The system of claim 1, wherein the fluid properties of the cleaning fluid are set by lowering the air pressure and the fluid flow rate respectively below a predetermined standard air pressure and a predetermined standard fluid flow rate.

11. The system of claim 1, wherein the input parameters of the small enclosed space are manually input.

12. The system of claim 1, wherein the input parameters of the small enclosed space are measured by a plurality of sensors that are in networked communication with the processing unit.

13. The system of claim 12, wherein the processing unit and the decontamination device are in wireless communication.

* * * * *